United States Patent
Anand et al.

(10) Patent No.: US 11,793,974 B2
(45) Date of Patent: Oct. 24, 2023

(54) FIXATION DEVICES FOR CATHETERS

(71) Applicant: ALCYONE THERAPEUTICS, INC., Lowell, MA (US)

(72) Inventors: P J Anand, Lowell, MA (US); Deep Arjun Singh, Cambridge, MA (US); Andrew East, Lowell, MA (US); Thomas T. Washburn, Lancaster, MA (US); Rahul Veetekat, Westborough, MA (US); Nicole Bettè, Lowell, MA (US); Chris Fleege, Villa Park, IL (US); Matthew J. Lapinski, Lowell, MA (US); Burt Raymond, Nashua, NH (US)

(73) Assignee: ALCYONE THERAPEUTICS, INC., Lowell, MA (US)

(*) Notice: Subject to any disclaimer, the term of this patent is extended or adjusted under 35 U.S.C. 154(b) by 79 days.

(21) Appl. No.: 16/788,192

(22) Filed: Feb. 11, 2020

(65) Prior Publication Data
US 2020/0254222 A1   Aug. 13, 2020

Related U.S. Application Data

(60) Provisional application No. 62/892,743, filed on Aug. 28, 2019, provisional application No. 62/804,032, filed on Feb. 11, 2019.

(51) Int. Cl.
*A61M 25/04*   (2006.01)
*A61M 25/02*   (2006.01)

(52) U.S. Cl.
CPC ....... *A61M 25/04* (2013.01); *A61M 2025/024* (2013.01); *A61M 2025/0206* (2013.01);
(Continued)

(58) Field of Classification Search
CPC .......... A61M 2025/0286; A61M 25/02; A61M 2025/0253; A61M 2025/0246;
(Continued)

(56) References Cited

U.S. PATENT DOCUMENTS

| | | | | |
|---|---|---|---|---|
| 4,553,961 A | * | 11/1985 | Pohndorf | A61B 17/11 604/175 |
| 4,662,873 A | * | 5/1987 | Lash | A61M 25/02 604/179 |

(Continued)

FOREIGN PATENT DOCUMENTS

| | | |
|---|---|---|
| DE | 202011002781 U1 | 5/2011 |
| JP | 2006305025 A | 11/2006 |

OTHER PUBLICATIONS

International Application No. PCT/US2020/017752, International Search Report and Written Opinion, dated Jun. 19, 2020.
(Continued)

*Primary Examiner* — Katherine H Schwiker
*Assistant Examiner* — Robert F Allen
(74) *Attorney, Agent, or Firm* — MARSHALL, GERSTEIN & BORUN LLP

(57) ABSTRACT

Fixation devices are disclosed herein that can be used to secure to a catheter. The fixation devices include a body having a central bore extending therethrough to receive a catheter and at least one end having a tapered profile tapering inwardly a distal edge thereof. The body can include an expanded intermediate portion, such as one or more bulbous portions. The fixation devices can also include suture openings or grooves to secure the devices to tissue.

18 Claims, 20 Drawing Sheets

(52) U.S. Cl.
CPC ............... *A61M 2025/028* (2013.01); *A61M 2025/0246* (2013.01); *A61M 2025/0253* (2013.01); *A61M 2025/0266* (2013.01); *A61M 2025/0286* (2013.01)

(58) Field of Classification Search
CPC .... A61M 2025/024; A61M 2025/0266; A61M 2025/028; A61M 2025/026; B65D 63/00
See application file for complete search history.

(56) References Cited

U.S. PATENT DOCUMENTS

| | | | | |
|---|---|---|---|---|
| 4,699,616 | A * | 10/1987 | Nowak | A61M 25/02 128/DIG. 26 |
| 4,874,380 | A * | 10/1989 | Hesketh | A61M 25/02 604/338 |
| 4,971,272 | A * | 11/1990 | Gudridge | F16L 3/137 24/17 AP |
| 5,395,343 | A | 3/1995 | Iscovich | |
| 5,423,763 | A * | 6/1995 | Helland | A61M 25/02 600/431 |
| 5,683,403 | A * | 11/1997 | Adams | A61N 1/05 606/151 |
| 5,824,032 | A * | 10/1998 | Belden | A61N 1/057 604/179 |
| 6,113,572 | A | 9/2000 | Gailey et al. | |
| 8,126,569 | B2 * | 2/2012 | Rivard | A61N 1/057 606/232 |
| 9,642,987 | B2 * | 5/2017 | Bierman | A61M 25/00 |
| 9,717,885 | B1 | 8/2017 | Narciso Martinez et al. | |
| 10,814,104 | B2 * | 10/2020 | Amon | A61M 25/02 |
| 2001/0011164 | A1 | 8/2001 | Bierman | |
| 2006/0064159 | A1 | 3/2006 | Porter et al. | |
| 2011/0118670 | A1 | 5/2011 | Dennis et al. | |
| 2014/0236198 | A1 | 8/2014 | Goldfarb et al. | |
| 2015/0038912 | A1 * | 2/2015 | Karim | A61M 25/02 604/178 |
| 2017/0050786 | A1 * | 2/2017 | Kozminkse | B65D 63/1027 |
| 2017/0136215 | A1 * | 5/2017 | Harders | A61M 25/02 |
| 2018/0318554 | A1 | 11/2018 | Karim et al. | |

OTHER PUBLICATIONS

European Patent Application No. 20755022, Extended European Search Report, dated Sep. 23, 2022.

* cited by examiner

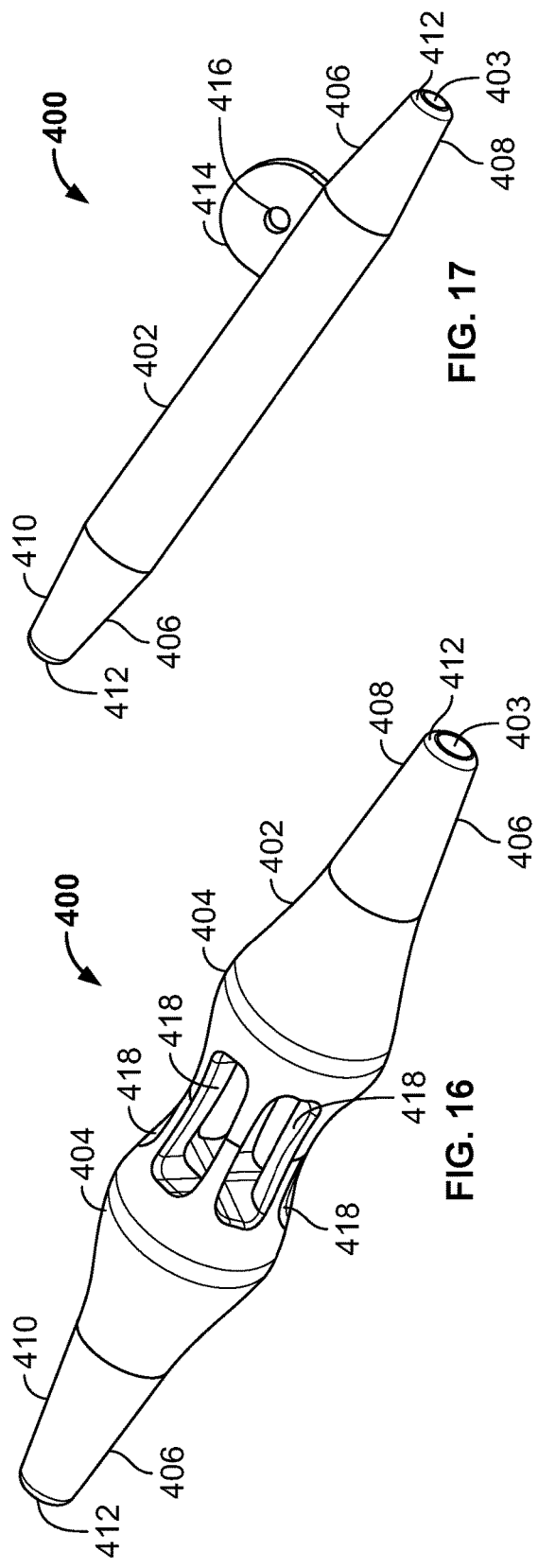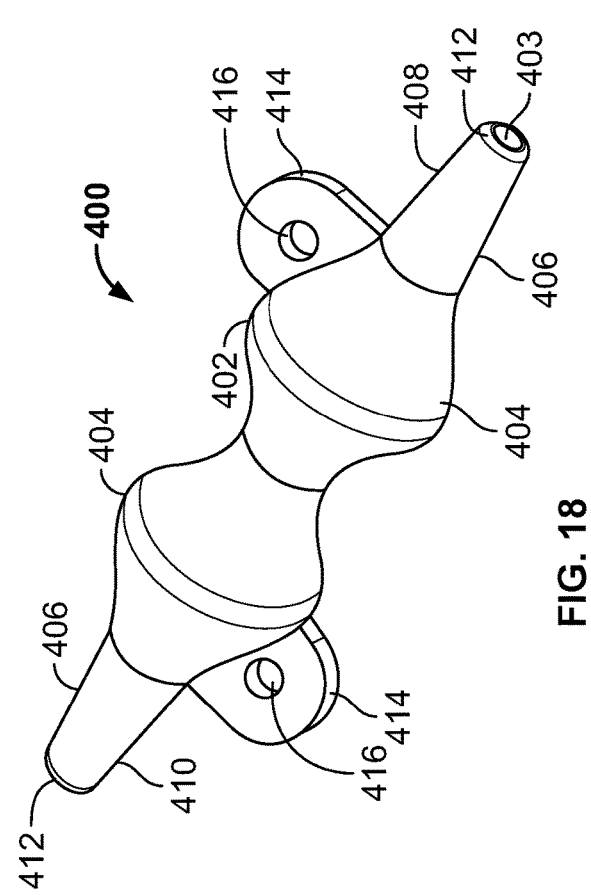

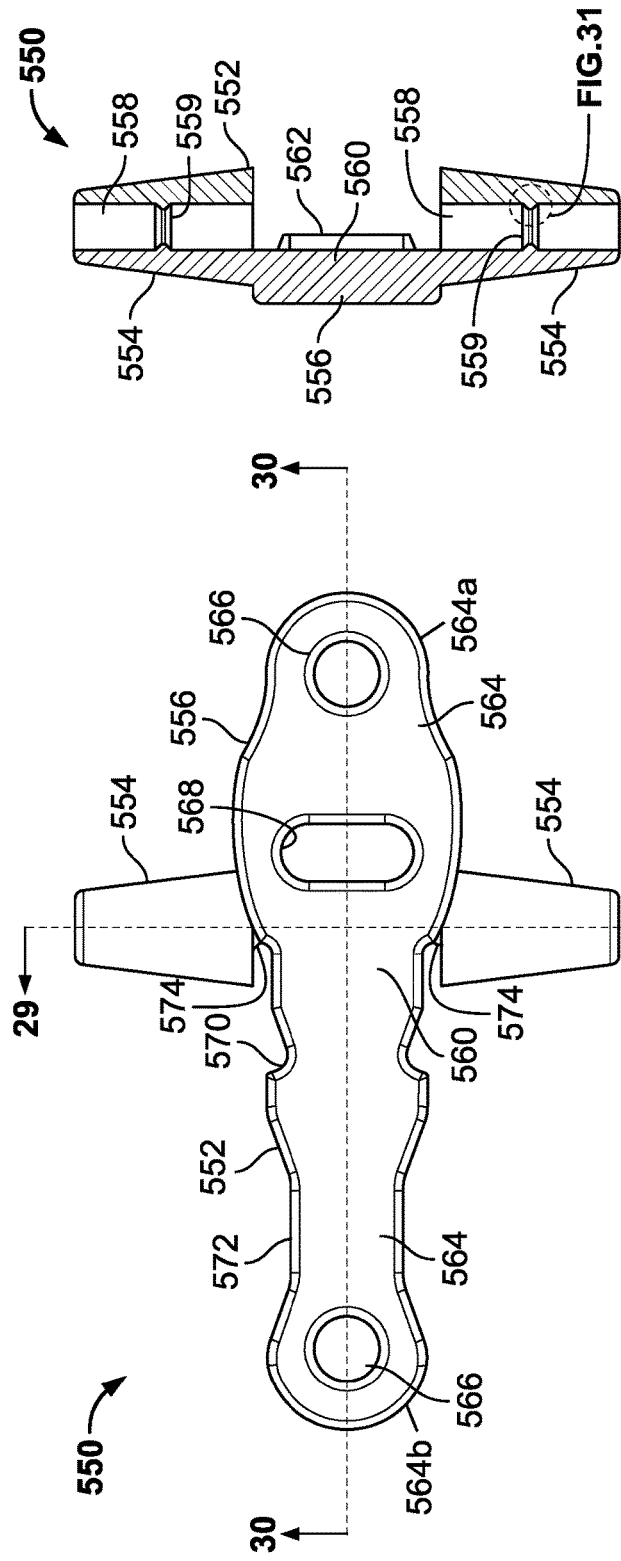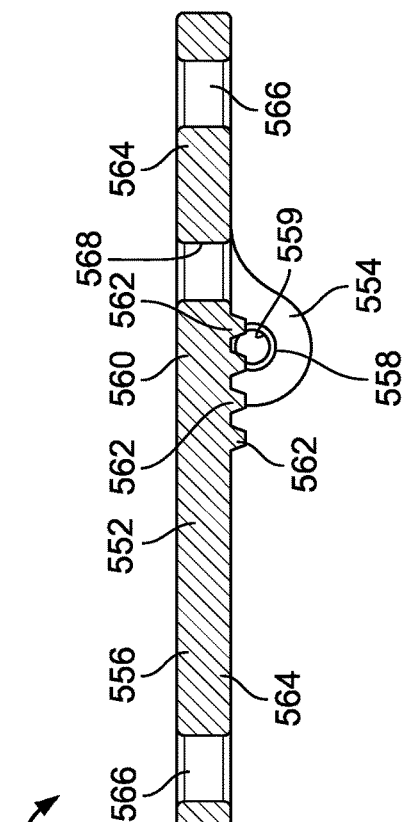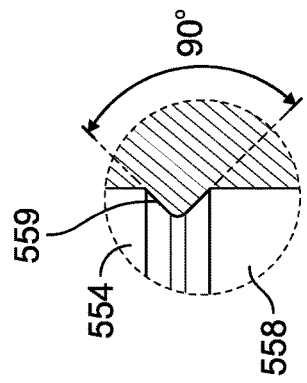

FIXATION DEVICES FOR CATHETERS

CROSS-REFERENCE TO RELATED APPLICATIONS

This application claims the benefit of U.S. Provisional Application No. 62/804,032, filed Feb. 11, 2019, and U.S. Provisional Application No. 62/892,743, filed Aug. 28, 2019, which are incorporated by reference herein in their entireties.

FIELD OF THE DISCLOSURE

The present disclosure generally relates to catheters and, more particularly, to fixation devices for catheters.

BACKGROUND

Applying sutures directly around an implantation opening for a catheter in the tissue of a patient can risk suture rupture, catheter lumen collapse, or even catheter tear, depending on the materials used for the catheter and the suture. These failures could, in turn, undesirably lead to catheter migration. For applications, such as intrathecal catheters, having long-term implantation and life, these risks may be further amplified.

SUMMARY

In accordance with a first aspect, a fixation device for a catheter is described herein that includes an elongate body having a central bore extending therethrough. An intermediate portion of the body has an expanded configuration and an end of the body has a tapered profile that tapers inwardly from the intermediate portion to a distal edge thereof.

According to some forms, the fixation device can include one or more of the following aspects: the body can include inwardly projecting catheter engagement protrusions; the expanded configuration can include a bulbous portion that extends outwardly from a generally central location of the body; the expanded configuration includes a plurality of bulbous portions giving the body an undulating outer surface; the end of the elongate body can be angled with respect to a longitudinal axis of the body or flexible, such that the end is adapted to be used as a plug in an opening in tissue; the body can be symmetrical, such that an opposite end of the body has a tapered profile tapering inwardly from the intermediate portion to a distal edge thereof; or the body can include one or more slot openings extending radially therethrough to the central bore.

According to some forms, the fixation device can include at least one tab that projects outwardly from the body and has a suture opening extending therethrough. In further forms, the at least one tab can be a plurality of tabs that are arrayed in an asymmetrical pattern about the body or the at least one tab can be a circular flange that extends outwardly from the body and has openings arranged about a circumference thereof. In one version, the circular flange can include slots that extend radially inwardly from edges thereof to define wedge portions that are adapted to be flexed to desired positions around a catheter.

According to some forms, the fixation device can further include a valve that extends across the central bore and is adapted to engage a catheter inserted therethrough to restrict movement of the catheter. In further forms, the central bore can include an expanded intermediate portion to allow portions of the valve to deflect therein due to a catheter being inserted therethrough. Moreover, the valve can be a one way valve or a toggle valve.

According to some forms, the body can include a longitudinal opening extending along at least a portion thereof; and the fixation device can further include opposing wings that extend laterally outwardly from edges of the longitudinal opening, where the wings are adapted to be secured together. In further forms, the wings can include opposing longitudinally opening slots that extend adjacent to the body, such that the wings are configured to latch together by interlocking the slots or the wings can be a male wing and a female wing, where the female wing includes a coupling slot that extend longitudinally across a width thereof and the male wing includes a notched portion having a width sized to fit within the coupling slot. In one version, the female wing can further include a second slot that extends laterally from the coupling slot, where the second slot is sized to receive the male wing therethrough so that the notched portion can be positioned within the coupling slot.

According to some forms, the body can include one or more grooves extending around at least a portion thereof. In further forms, the fixation device can include a clamp member having one or more protrusions that are adapted to be inserted into the one or more grooves as the clamp member is secured around the body. The clamp member can be configured to compress the body around a catheter inserted therethrough.

In accordance with a second aspect, a fixation device for a catheter is described that includes an elongate band having a suture opening extending therethrough. The elongate band includes a female end having a coupling opening extending therethrough and an opposite, male end. A retention portion of the male end is configured to be inserted into the coupling opening of the female end to thereby secure the elongate band around a catheter.

According to some forms, the elongate band can have a rigid configuration with the male end curved back over the female end to define an open bore to receive a catheter therein and the retention portion can be configured to snap-fit within the slot opening with the male end flexed toward the female end to secure the elongate band to the catheter.

According to some forms, the elongate band can be a first elongate band and the device can include a second elongate band having a suture opening extending therethrough and a central strip extending longitudinally between and connecting the first and second elongate bands together. The second elongate band can include a female end having a coupling opening extending therethrough and an opposite, male end. A retention portion of the male end of the second elongate band can be configured to be inserted into the slot opening of the female end to thereby secure the second elongate band around a catheter. The device can be configured so that the male ends of the first and second elongate bands are disposed on opposite sides of the central strip, such that the device defines a tortuous path for the catheter with the retention portions secured within the respective coupling openings.

According to any of the above forms, a catheter engagement portion of the elongate band can include textured surfaces.

In accordance with a third aspect, a fixation device for a catheter is described herein that includes a sleeve member having a central portion and a bore extending longitudinally therethrough. The fixation device further includes a collar member having an annular body sized to fit over and compress the central portion of the sleeve member and one or more tabs that extend outwardly from the collar member. The one or more tabs each have a suture opening extending therethrough.

According to some forms, the sleeve member can include a longitudinal slit that extends through a side thereof to the bore, such that the sleeve member can be longitudinally opened to be disposed around a catheter.

According to some forms, the sleeve member can include barbed retention ends on opposite sides of the central portion. In further forms, the collar member can include portions spaced longitudinally from the retention ends of the sleeve member to define suture gaps therebetween with the collar member mounted therearound; and/or the retention ends can have inwardly tapered profiles.

BRIEF DESCRIPTION OF THE DRAWINGS

The above needs are at least partially met through provision of the embodiments described in the following detailed description, particularly when studied in conjunction with the drawings, wherein:

FIG. 16 is a perspective view of an tenth example fixation device for a catheter in accordance with various embodiments;

FIG. 17 is a perspective view of a eleventh example fixation device for a catheter in accordance with various embodiments;

FIG. 18 is a perspective view of a twelfth example fixation device for a catheter in accordance with various embodiments;

FIG. 28 is a top plan view of a eighteenth example fixation device for a catheter in accordance with various embodiments;

FIG. 29 is a cross-sectional view of the fixation device of FIG. 28 taken along the line 29-29;

FIG. 30 is a cross-sectional view of the fixation device of FIG. 28 taken along the line 30-30;

FIG. 31 is a sectional view of a portion of FIG. 30;

DETAILED DESCRIPTION

Fixation devices, which can include fixation tabs, suture wings, or anchoring wings, are disclosed herein that can be used to secure to a catheter and optionally secure a catheter in place with the use of sutures. The fixation devices can aid in preventing catheter migration or dislodgement from an implantation site. For intrathecal applications, the fixation devices disclosed herein can be implantable for relatively long-term periods to secure or anchor the catheter to the fascia of the patient after the catheter has been implanted in the intrathecal space. In one approach, a tip of the fixation device can be used to plug the opening in the dura at the insertion site.

The fixation devices disclosed herein can advantageously provide one or more of the following aspects: fit snugly over the outer diameter of the catheter without compressing the catheter's inner diameter, not rely solely on sutures for securing onto the catheter, stay in place once secured without sliding back and forth regardless of wet conditions, anchor the catheter to the fascia with the use of sutures, serve to plug the hole at the dura to reduce the risk of cerebrospinal fluid (CSF) leakage, not stick out perpendicularly to the fascia in a way that could lead to tissue erosion, withstand sutures without breaking or abrading, be radiopaque, be safe, biocompatible, and long-lasting to function as a long-term implantable device, be able to be used at any desired anchoring site, including, for example, at the dura, away from the dura, and in the subcutaneous port pocket, and be suitable for mass manufacture. In some versions, the fixation devices described herein can further provide one or more of the following aspects: be able to be repositioned once placed, be able to be placed without the use of a dispensing tool, be symmetrical so that a user can place the device without concern about orientation and so that the device does not have to be removed and redeployed after it has been deployed.

Figure 1:
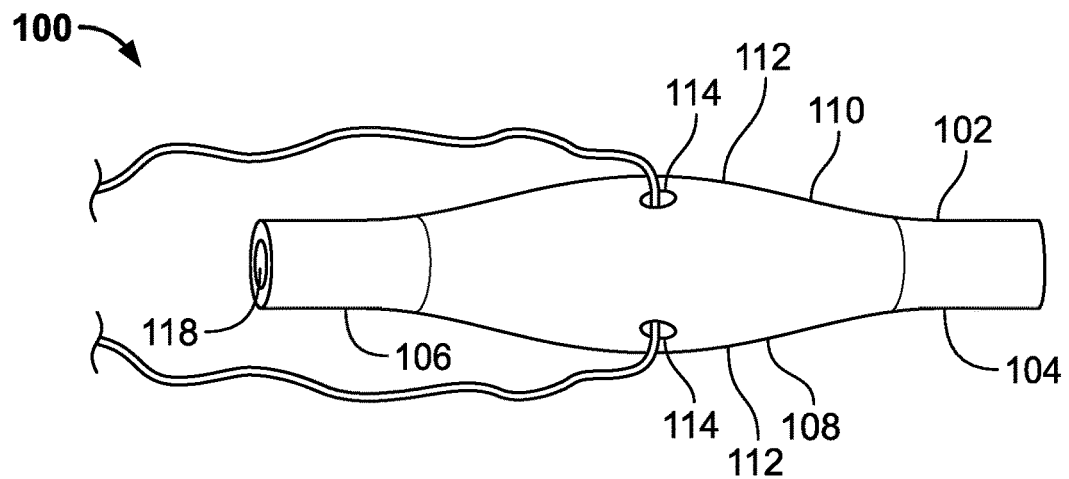
FIG. 1 is a sectional view of a first example fixation device for a catheter in accordance with various embodiments.
Figure 2:
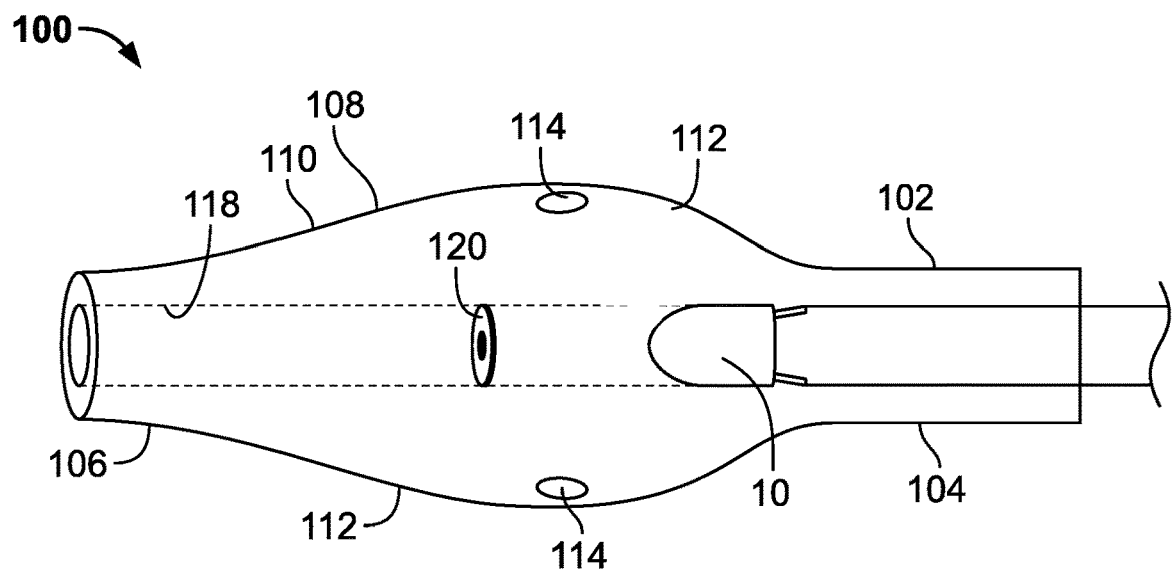
FIG. 2 is a cross-sectional view of the fixation device of FIG. 1.
Figure 3:
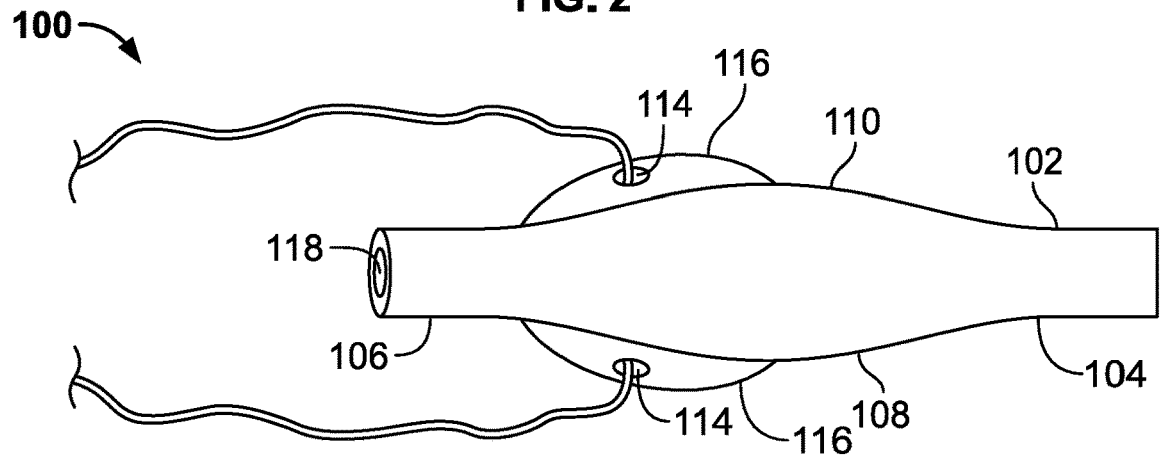
FIG. 3 is a sectional view of a second example fixation device for a catheter in accordance with various embodiments.

A first example fixation device 100 is shown in FIGS. 1 to 3. The fixation device 100 of this form includes an elongate body 102 with a proximal end 104 and a distal end 106. The body 102 has an outwardly bulging intermediate or central portion 108. The bulging portion 108 can preferably have a curved or tapered profile so that the body 102 has a smooth outer surface 110 transitioning from the proximal end 104, over the bulging portion 108, and to the distal end 106. The tapered profile of the body 102 extending to the distal end 106 from the intermediate portion 108 can advantageously be utilized to act as a plug when a user inserts the distal end 106 into the opening through the dura of a patient. The inwardly tapered profile of the distal end 106 seals with the dura in the opening therethrough to prevent or minimize the leakage of CSF. If desired, the body 102 can be symmetrical so that the proximal and distal ends 104, 106 have similarly tapered profiles and can each be used as a plug. This allows a user to implant the device 100 without having to worry about orientation.

In one version, the bulging portion 108 includes wings 112 extending laterally outwardly on opposite sides of the body 102. In another version, the bulging portion 108 can extend around an entire circumference of the body 102. The bulging portion 108 further includes suture openings 114 that extend generally transverse to a longitudinal axis L of the body 102. In an alternative version as shown in FIG. 3, the body can further include tabs 116 extending outwardly from opposite sides of the body 102 and on the distal end side of the bulging portion 108. In this form, the tabs 116 include the suture openings 114. The tabs 116 are longitudinally spaced from the distal end 106 so that the end 106 can be utilized as a plug as described above.

Turning now to FIG. 2, the body 102 includes a central bore 118 extending longitudinally therethrough along the longitudinal axis L that is sized to receive a catheter 10. While the device 100 may be suitable for many purposes in this form, the device 100 can further include one or more one-way valves 120 extending across the inner diameter of the central bore 118. The valves 120 are configured to allow the catheter 10 to only move in a single direction therethrough and, thus, through the body 102. Accordingly, the valves 120 allow a user to insert the catheter 10 through the body 102, but thereafter resist or prevent retrograde slippage of the catheter 10 through the device 100.

With any of the above versions, after a user has implanted the catheter 10, a user can then advance the fixation device 100 over the catheter 10 to a final desired position. Then, the user can suture the device 100 in place using the openings 114 to prevent the catheter 10 from migrating. The device 100 can be sutured in any desired location, including to the fascia at the site of the dura entry, away from the dura, e.g., Scarpa's fascia, in a port pocket, and so forth.

Figure 4:
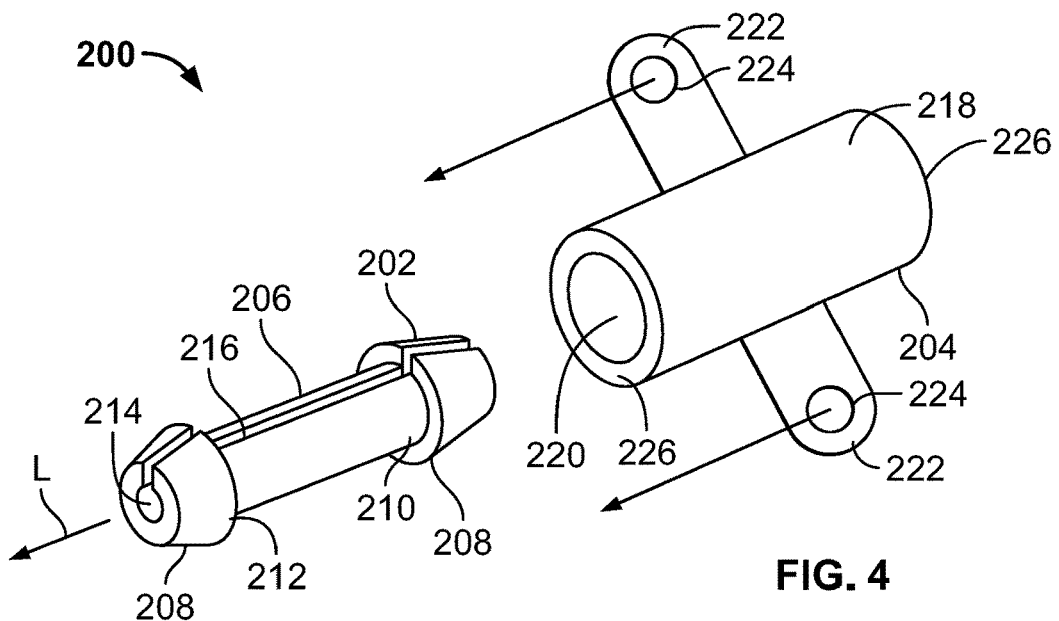
FIG. 4 is a schematic perspective view of a third example fixation device for a catheter in accordance with various embodiments.
Figure 5:
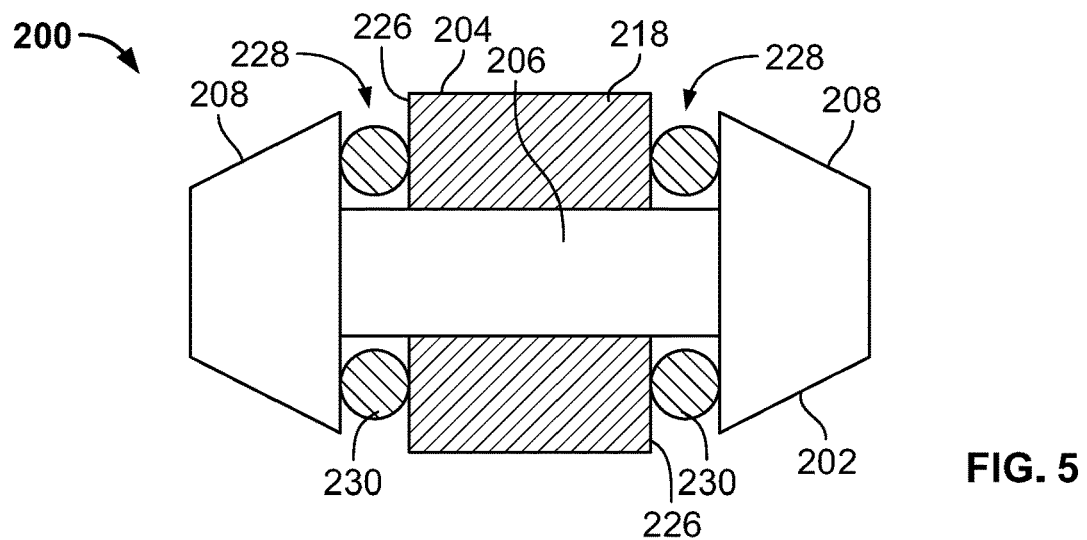
FIG. 5 is a cross-sectional view of the fixation device of FIG. 4.
Figure 6:
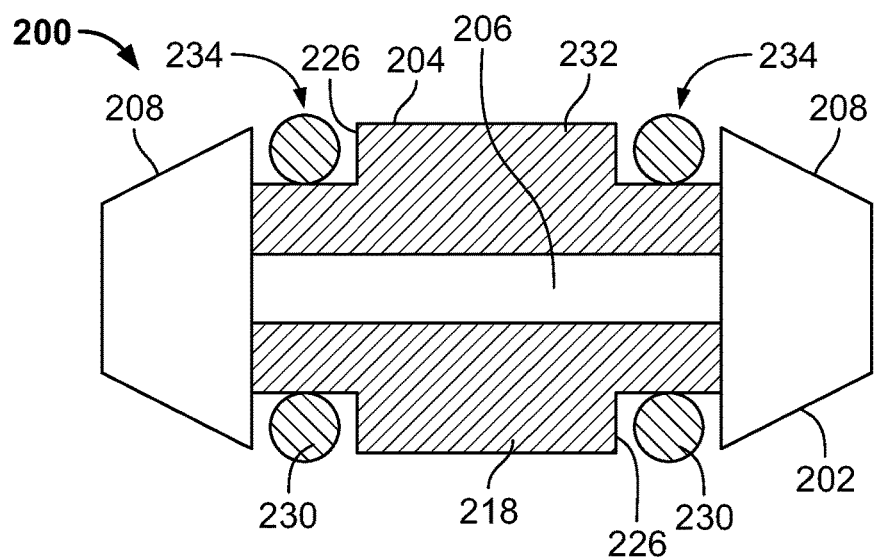
FIG. 6 is a cross-sectional view of an alternative outer member for the fixation device of FIG. 4.

Another example fixation device 200 is shown in FIGS. 4 to 6. The fixation device 200 of this form has a two-piece design with an inner sleeve member 202 and an outer collar member 204. The sleeve 202 and collar 204 can be used in combination to create a seal around a catheter 10 to thereby prevent fluid from passing around the catheter 10 or allow the catheter 10 to move axially with respect to the device 200.

The sleeve 202 includes a central cylindrical body 206 with outwardly extending barbed retention portions 208 at proximal and distal ends 210, 212 thereof. In the illustrated form, the retention portions 208 have frusto-conical shapes oriented so that the retention portions 208 taper radially inwardly towards ends of the sleeve 202. Of course, other shapes can be utilized, including cylindrical, curved, and so forth. As shown, the sleeve 202 includes a central bore 214 extending longitudinally therethrough along a longitudinal axis L that is sized to receive a catheter 10.

The sleeve 202 can be composed of a soft flexible material, such as a low durometer silicone, that allows a user to resiliently deform the sleeve 202 for implantation. In one form, the sleeve 202 can include a longitudinal slit 216 that extends radially through a side of the sleeve 202 to the central bore 214. With this configuration, a user can separate the sleeve 202 along the slit 216 to thereby position the catheter 10 within the central bore 214 at a desired location of the catheter 10. Thereafter, the sleeve 202 will resiliently return to its original shape so that the sleeve 202 extends around the catheter 10. In another form, the sleeve 202 can be advanced along the length of the catheter 10 until a desired location is reached, instead of using the slit 216.

The collar 204 includes an annular body 218 with a central bore 220 extending therethrough and tabs 222 extending laterally from the body 218. The tabs 222 each include a suture opening 224 extending therethrough. The collar 204 can be composed of a soft flexible material, such as a medium to higher durometer silicone, so that a user can stretch the collar over the sleeve 202 to assemble the fixture device 200. Further, the collar 204 can be sufficiently resilient to provide a sufficient amount of hoop stress on the sleeve 202 to seal off and hold the catheter 10 within the device 200. In one form, the body 218 of the collar 204 can be sized so that a length thereof is equal to or slightly, e.g., between about 1 mm to about 5 mm or between about 1 mm to about 3 mm, smaller than a distance between the retention portions 208 of the sleeve 202. In another form as shown in FIG. 5, the body 218 of the collar 204 can be sized so that ends 226 of the body 218 are spaced from the retention portions 208 by gaps 228. These gaps 228 advantageously provide a protected and secure location to receive sutures or ligatures 230 to secure the fixture device 200 to a patient's tissue at a desired location, such as to the facia at the site of the dura entry, away from the dura, e.g., Scarpa's facia, in a port pocket, and so forth. In another form as shown in FIG. 6, the collar 204 can include an intermediate portion 232 that extends radially outwardly from adjacent portions of the collar 204. Further, the body 218 can have a length equal to or slightly smaller than the distance between the retention portions 208 of the sleeve 202. With this configuration, gaps 234 are created between the intermediate portion 232 and the respective retention portion 208 of the sleeve 202, while the longitudinal ends of the sleeve 202 extend across bottoms of the gaps 234. This arrangement prevents sutures or ligatures 230 from directly contacting the sleeve 202.

So configured, a user can position the sleeve 202 at a desired location on the catheter 10, either by threading the sleeve 216 along the length of the catheter or by installing the sleeve 202 on the catheter with the slit 216. After the sleeve 202 is placed at the desired location, a user can then thread the collar 204 from the proximal end of the catheter 10 down to the sleeve 202. Then the user can deform the collar 204 and place the collar 204 into position between the retention ends 208 of the sleeve 202. An outer diameter of the sleeve 202 and an inner diameter of the collar 204 can advantageously be sized and configured to create an interference fit that provides a desired hold on the catheter 10 to restrict or prevent the catheter 10 from migrating. The user can then place sutures through the openings 224 to fix or secure the assembly to surrounding tissue and/or place sutures through the gaps 228, 234. In an alternative form, the sleeve 202 can include tabs that project outwardly of the collar 204 with suture openings. Moreover, the fixture device 200 can be provided with a deployment tool (not shown) that aids in stretching the collar 204 over the sleeve 202 and/or placing the assembled fixture device into surgically hard to reach locations. The sleeve 202 and/or collar 204, or portions thereof, can be loaded with barium sulphate (BaSO4) or other suitable radiopaque material so that the radiopaque portions can be imaged using conventional X-ray techniques.

Figure 7:
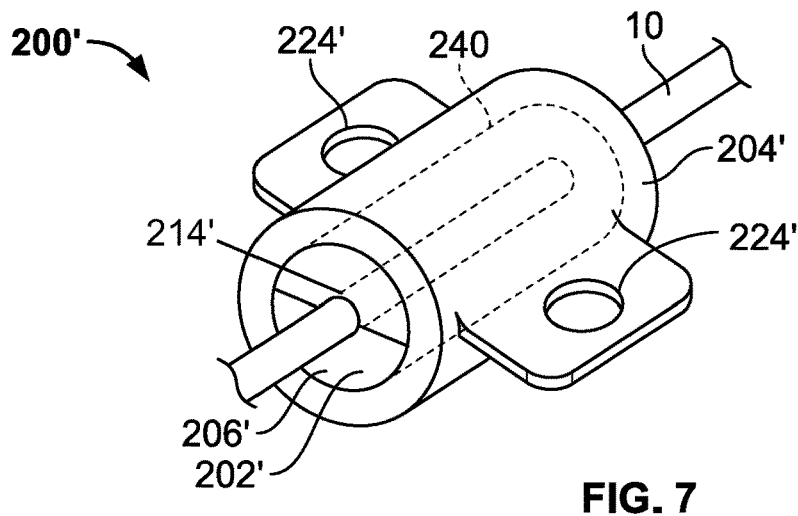
FIG. 7 is a perspective view of a fourth example fixation device for a catheter in accordance with various embodiments.

In another example shown in FIG. 7, a fixation device 200' can include a sleeve 202' with only a central cylindrical body 206' without the barbed retention portions 208. As shown, the sleeve 202' can include a central bore 214' extending longitudinally therethrough along the longitudinal axis L that is sized to receive a catheter 10. In this form, an outer diameter of the sleeve 202' and an inner diameter of a collar 204' can advantageously be sized and configured to create an interference fit that provides a desired hold on the catheter 10 to restrict or prevent the catheter 10 from migrating. The user can then place sutures through one or more openings 224' to fix or secure the assembly to surrounding tissue. If desired, the sleeve 202' can have a longitudinal slit and a clamshell configuration with a longitudinal hinged connection 240 or can have a two-piece construction, so that the sleeve 202' can be positioned on the catheter 10 at a desired location and the collar 204' can be disposed over the sleeve 202' to couple the device 200' to the catheter 10.

Figure 8:
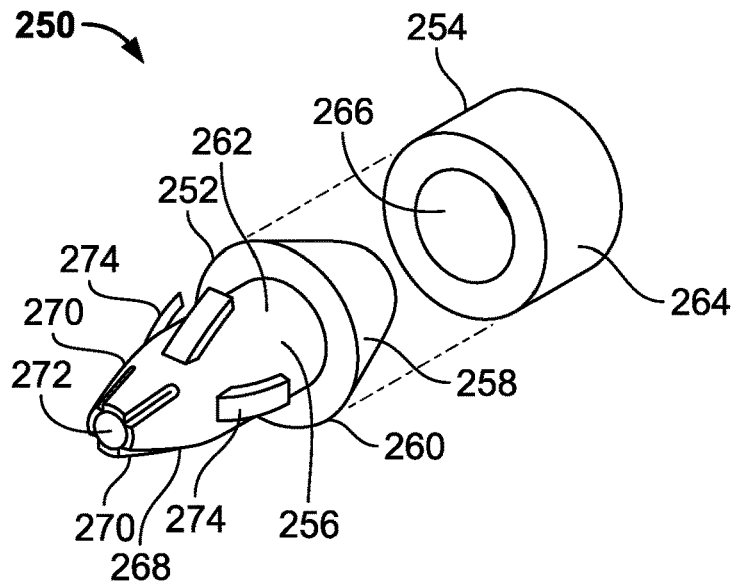
FIG. 8 is an exploded view of a fifth example fixation device for a catheter in accordance with various embodiments.
Figure 9:
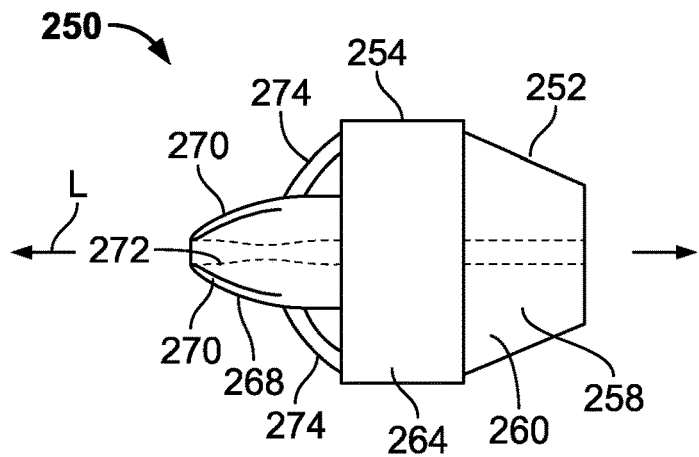
FIG. 9 is a side elevational view of the fixation device of FIG. 8 in an assembled configuration.

In yet another example, a fixation device 250 is shown in FIGS. 8 and 9. The fixation device 250 of this form has a two-piece design with an inner sleeve member 252 and an outer collar member 254. The sleeve 252 and collar 254 can be used in combination to create a seal around a catheter 10 to thereby prevent fluid from passing around the catheter 10 or allow the catheter 10 to move axially with respect to the device 250.

The sleeve 252 includes a generally cylindrical body 256 with an outwardly extending barbed retention portion 258 at a proximal end 260. As shown, the retention portion 258 has an increased diameter relative to an intermediate portion 262 of the sleeve 252. With this configuration, the retention portion 258 prevents the collar 254 from migrating off of the proximal end 260 of the sleeve 252. If desired, the retention portion 258 can have a frusto-conical shape oriented so that the retention portion 258 tapers radially inwardly towards ends of the sleeve 252. Of course, other shapes can be utilized, including cylindrical, curved, and so forth.

The collar 254 includes an annular body 264 with a central bore 266 extending therethrough. If desired, the collar 254 can include tabs, configured similar to the above forms, that extend laterally from the body 264 and include a suture opening. The collar 254 can be composed of a soft flexible material, such as a medium to higher durometer silicone, so that a user can stretch the collar 254 over the sleeve 252 to assemble the fixture device 250. Further, the collar 254 can be sufficiently resilient to provide a sufficient amount of hoop stress on the sleeve 252 to seal off and hold the catheter 10 within the device 250.

A distal end 268 of the sleeve 252 has a longitudinally segmented configuration with a plurality of spaced-apart members 270, such as three or four members, forming the distal end 268. As shown, the sleeve 252 includes a central bore 272 extending longitudinally therethrough along a longitudinal axis L that is sized to receive a catheter 10. In a resting configuration, the members 270 can define a diameter therebetween for the central bore 272 that allows the catheter 10 to be slid through the sleeve 252 to allow a user to position the sleeve 252 on a desired portion of the catheter 10. Moreover, each of the members 270 can include an outwardly extending finger 274 configured so that the collar 254 is retained between the fingers 274 and the retention portion 258. By one approach, the fingers 274 can be angled to extend rearwardly along the sleeve 252 toward the proximal end 260 thereof. With this configuration, and the flexible nature of sleeve 252 with the spaced-apart members 270, the collar 254 can deflect the fingers 274 when the collar 254 is mounted to the sleeve 252. The deflection of the fingers 274 drives the members 270 inwardly to compress onto the catheter 10, which causes the fixation device 250 to secure to the catheter 10. An amount of deflection can be controlled by the stiffness of the material of the sleeve 252, including the members 270 and fingers 274, and the size of the fingers 274 relative to the collar 254 and the spacing between the fingers 274 and the retention portion 258.

Figure 10:
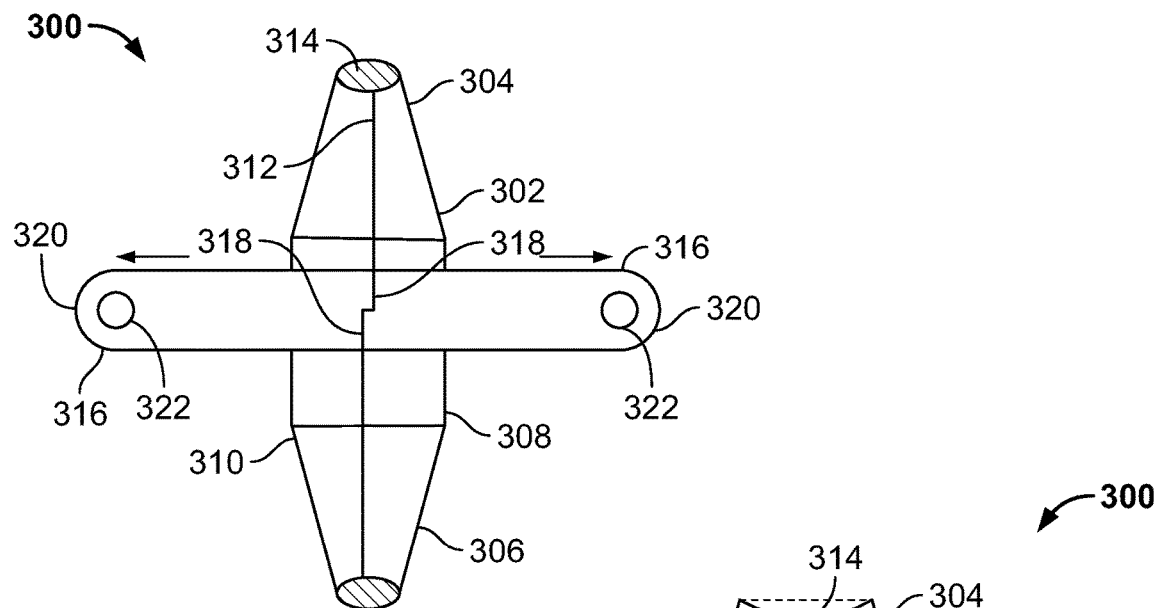
FIG. 10 is a top plan view of a sixth example fixation device for a catheter in accordance with various embodiments.
Figure 11:
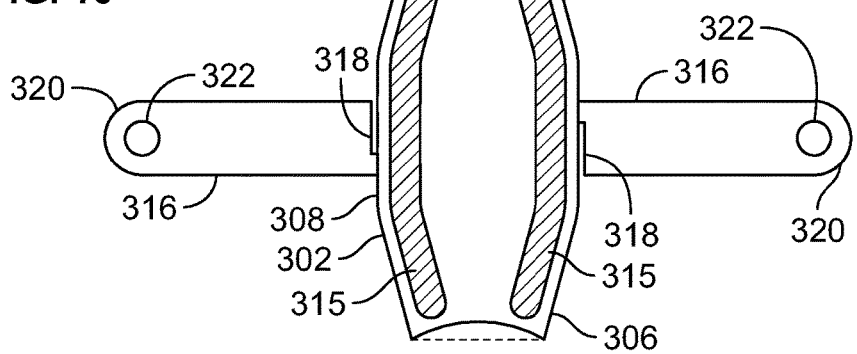
FIG. 11 is a top plan view of the fixation device of FIG. 10 in an open configuration.
Figure 12:
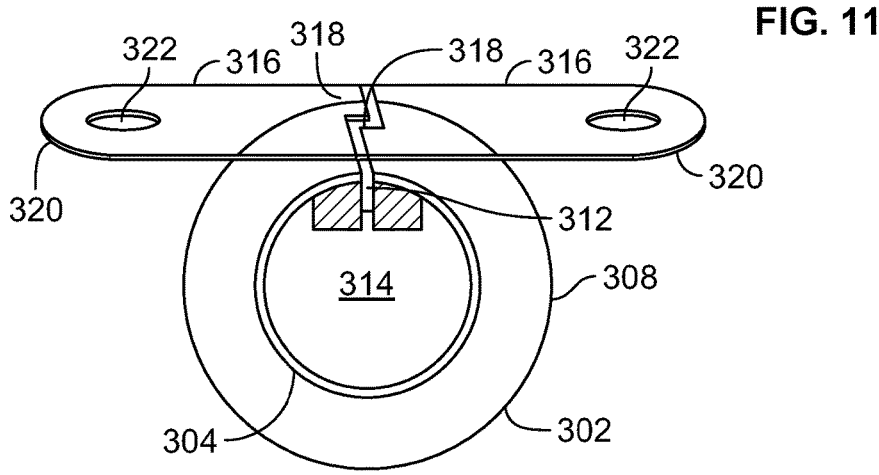
FIG. 12 is a front elevational view of the fixation device of FIG. 10.

Another example fixation device 300 is shown in FIGS. 10 to 12. The fixation device 300 of this form includes an elongate main body 302 with a proximal end 304 and a distal end 306. The body 302 has an outwardly bulging intermediate or central portion 308. The bulging portion 308 can preferably have a curved or tapered profile so that the body 302 has a smooth outer surface 310 transitioning from the proximal end 304, over the bulging portion 308, and to the distal end 306. The tapered profile of the body 302 extending to the distal end 306 can advantageously be utilized to act as a plug when a user inserts the distal end 306 into the opening through the dura of a patient. The inwardly tapered profile of the distal end 306 seals with the dura in the opening therethrough to prevent or minimize the leakage of CSF. If desired, the body 302 can be symmetrical so that the proximal and distal ends 304, 306 have similarly tapered profiles and can each be used as a plug. This allows a user to implant the device 300 without having to worry about orientation. Moreover, in some versions, one or both of the ends 304, 306 can be angled with respect to horizontal so that the end 304, 306 can extend into the dura opening while the remaining portion of the body 302 extends along or lies flat against the fascia.

As shown in FIGS. 10 to 12, the body 302 further includes a slit or opening 312 extending along a longitudinal length thereof so that the body 302 can be opened to expose an interior bore 314. In some versions, the body 302 can include teeth, ribs, or other textured surfaces 315 running along a portion of the interior bore 314 to grip a catheter 10 inserted therein. This configuration allows a user to place the body 302 around a desired portion of the catheter 10 without having to thread the body 302 along a length thereof.

The fixation device 300 further includes tabs or wings 316 that extend outwardly from opposite sides of the opening 312 in a generally central location. As shown in FIG. 11, connections between the tabs 312 and the body 302 include longitudinally opening slits 318. Specifically, one of the connections includes a slit 318 that opens towards the proximal end 304 and the other one of the connections includes a slit 318 that opens towards the distal end 306. With this configuration, a user can wrap the body 302 around the catheter 10 and latch the slits 318 to lock the tabs 316 together. Moreover, as the tabs 316 are pulled in opposite directions to latch the slits 318, the body 302 tightens around the catheter 10 causing the teeth 315 to press against the outer diameter of the catheter 10. Outer tips 320 of the tabs 318 can include openings 322 extending therethrough to receive sutures to secure the fixture device 300 to tissue. A further suture can be added around the tabs 316 to prevent them from coming apart.

Additional example fixation devices 400 are shown in FIGS. 13 to 20. The fixation devices 400 of these forms include a variety of structural features and functionalities that can be used individually or in combination with each other to achieve the design intent of sealing to the outer diameter of the catheter to prevent fluid from leaking between the fixation device 400 and catheter and/or to hold or secure the catheter in place.

In some examples, the fixture devices 400 have bodies 402 having a central bore 403 extending longitudinally therethrough to receive a catheter. The bodies 402 can include bulbous or ring-shaped portions 404 in single or multiple profiles that act as a plug to seal or prevent fluid leaks, such as a CSF leak from the opening through the dura. For example, as shown in the devices 400 of FIGS. 14-16 and 18-20, the body 402 can include bulbous portions 404 on either side of a body center, giving the body 402 a symmetric shape. The bulbous portions 404 can be used in combination with tapered end sections 406 that taper down to proximal and distal ends 408, 410 of the bodies 402. As shown, the tapered end sections 406 taper downwardly so that tips 412 thereof are slightly, e.g., between about 1 mm to 3 mm, larger than an outer diameter of the catheter due to a wall thickness of the body 402.

The fixture devices 400 can also include outwardly extending tabs 414 having openings 416 extending therethrough that allow for easy placement of sutures to secure the fixation devices 400 and catheter to surrounding tissue. One or two tabs 414 can be centrally located along the body 402, shown in the device 400 of FIGS. 13 and 19, for example, and/or can be located adjacent to one or both of the proximal and distal ends 408, 410, shown in devices 400 of FIGS. 17, 18, and 20. As shown, the tabs 414 can be provided in singular or in multiple locations or in opposing or asymmetric locations. Further, the tabs 414 can be extend from adjacent bulbous portions 404 in a web-like matter.

Figure 13:
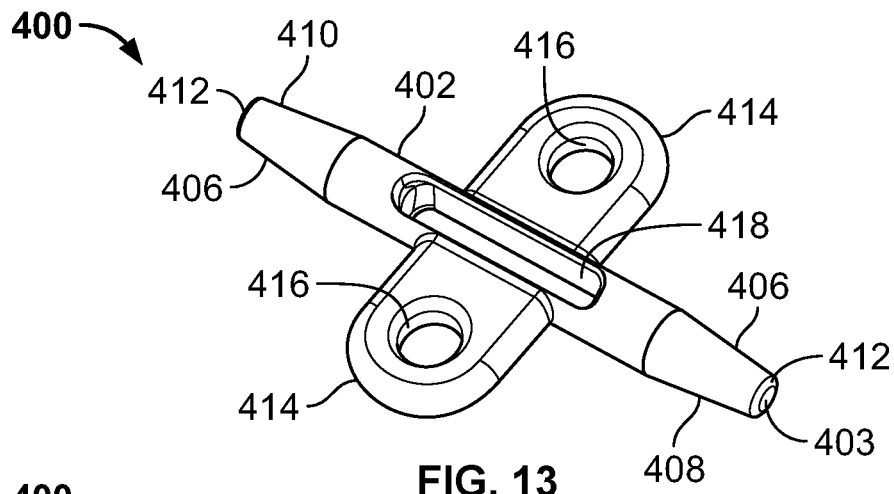
FIG. 13 is a perspective view of a seventh example fixation device for a catheter in accordance with various embodiments.
Figure 14:
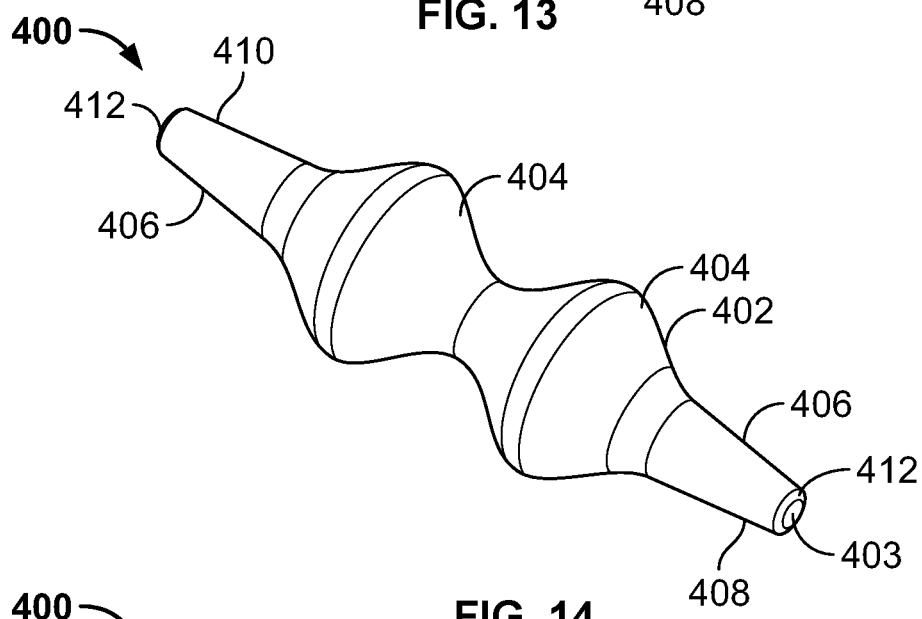
FIG. 14 is a perspective view of a eighth example fixation device for a catheter in accordance with various embodiments.
Figure 15:
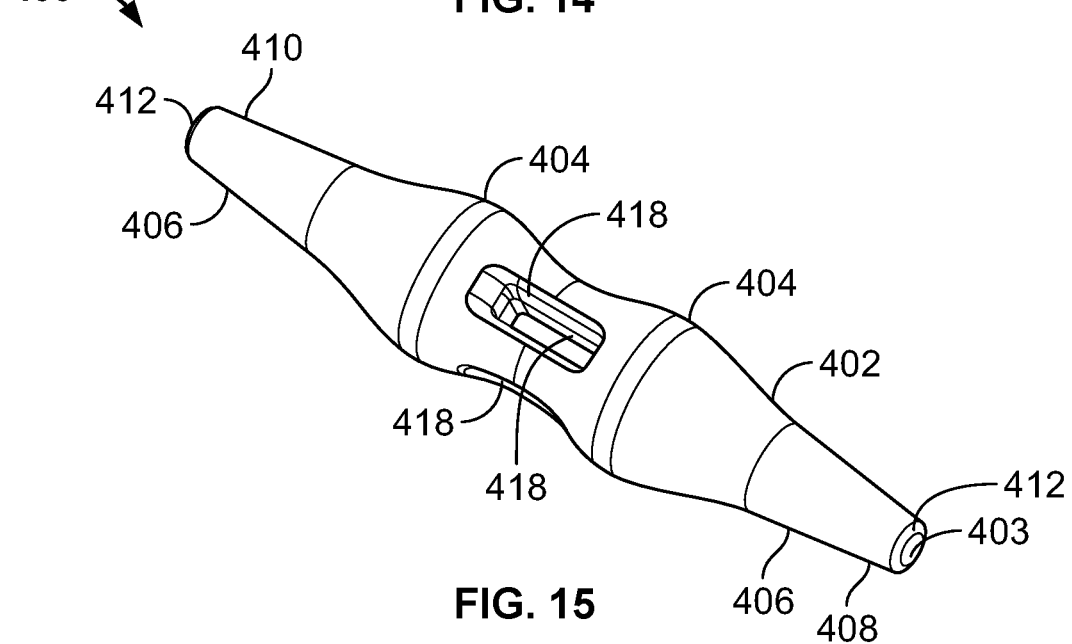
FIG. 15 is a perspective view of a ninth example fixation device for a catheter in accordance with various embodiments.
Figure 19:
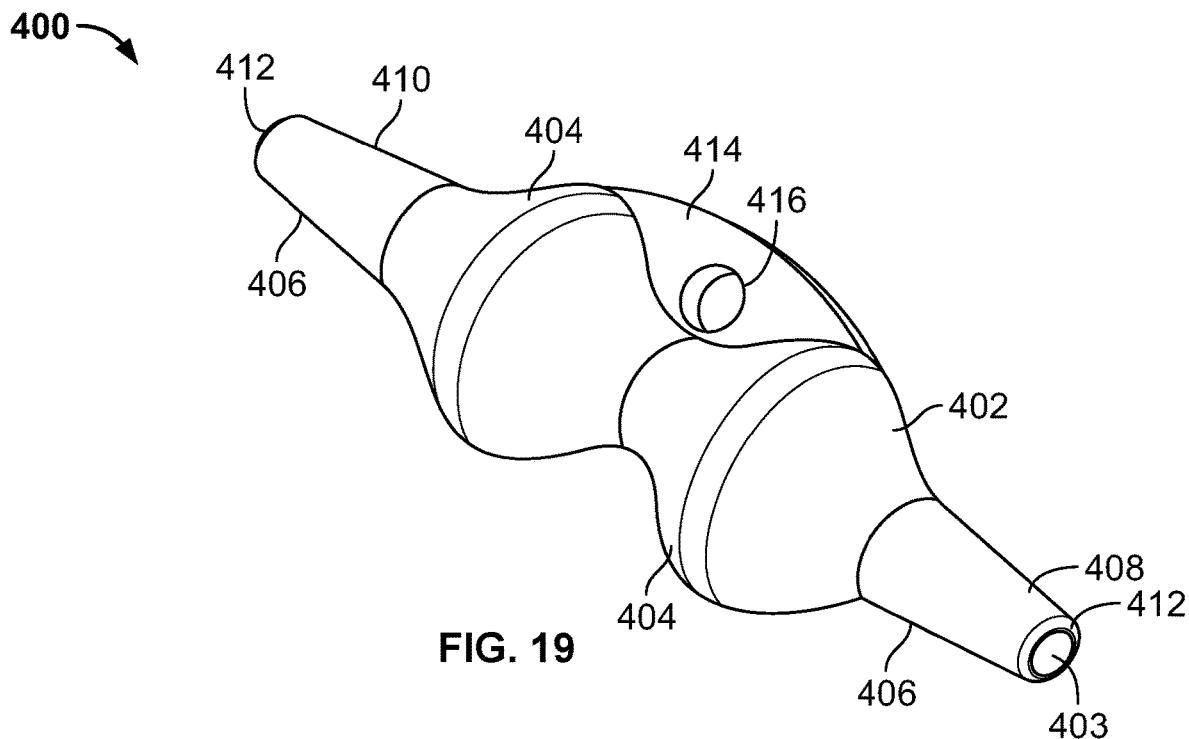
FIG. 19 is a perspective view of an thirteenth example fixation device for a catheter in accordance with various embodiments.
Figure 20:
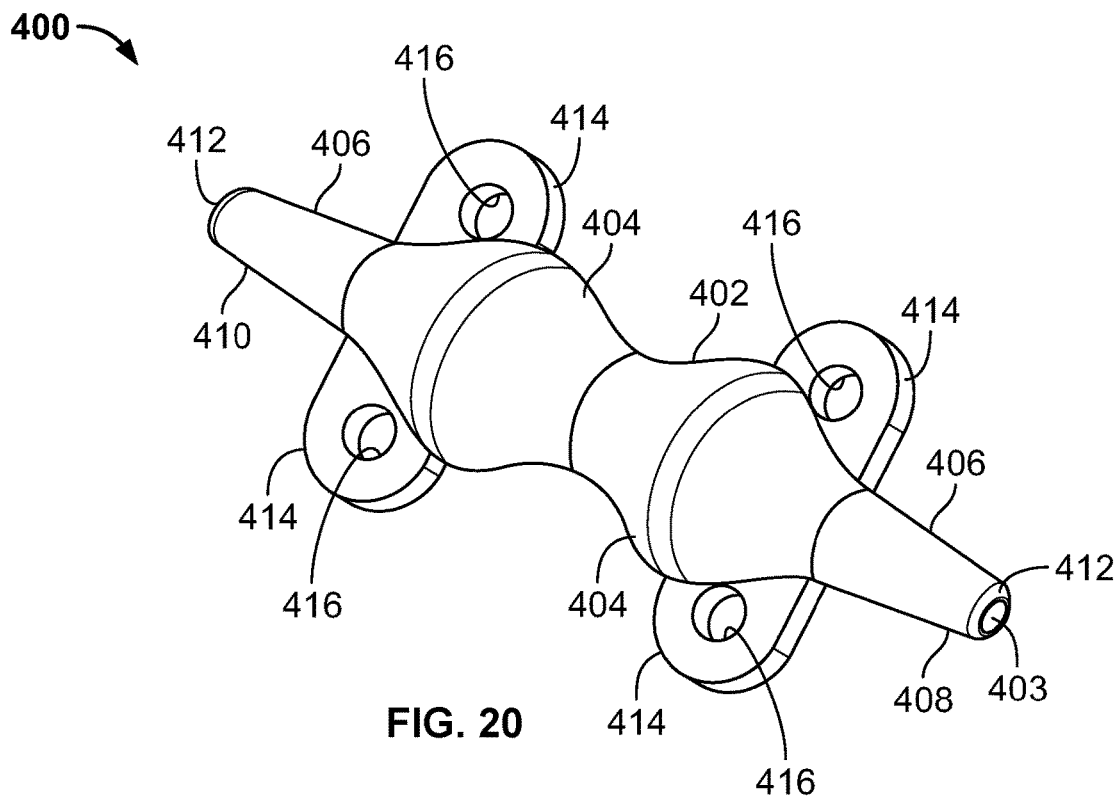
FIG. 20 is a perspective view of a fourteenth example fixation device for a catheter in accordance with various embodiments.

In some versions, the devices 400 can also include slots or cut-outs 418 that extend through the body 402 to the central bore 403. The slots 418 extend along an intermediate portion of the body 402 between the proximal and distal ends 408, 410. The devices 400 can include one slot 418, opposing slots 418 as shown in FIG. 13, four slots 418 disposed symmetrically around the body 402 as shown in FIG. 15, six slots 418 disposed symmetrically around the body 402 as shown in FIG. 16, or other numbers or patterns. The slots 418 allow for the catheter to be visualized therethrough and/or can be used to receive a suture or ligature to fix the device 400 to tissue and/or tighten around the catheter to increase the hold or sealing of the catheter within the device 400.

Figure 21:
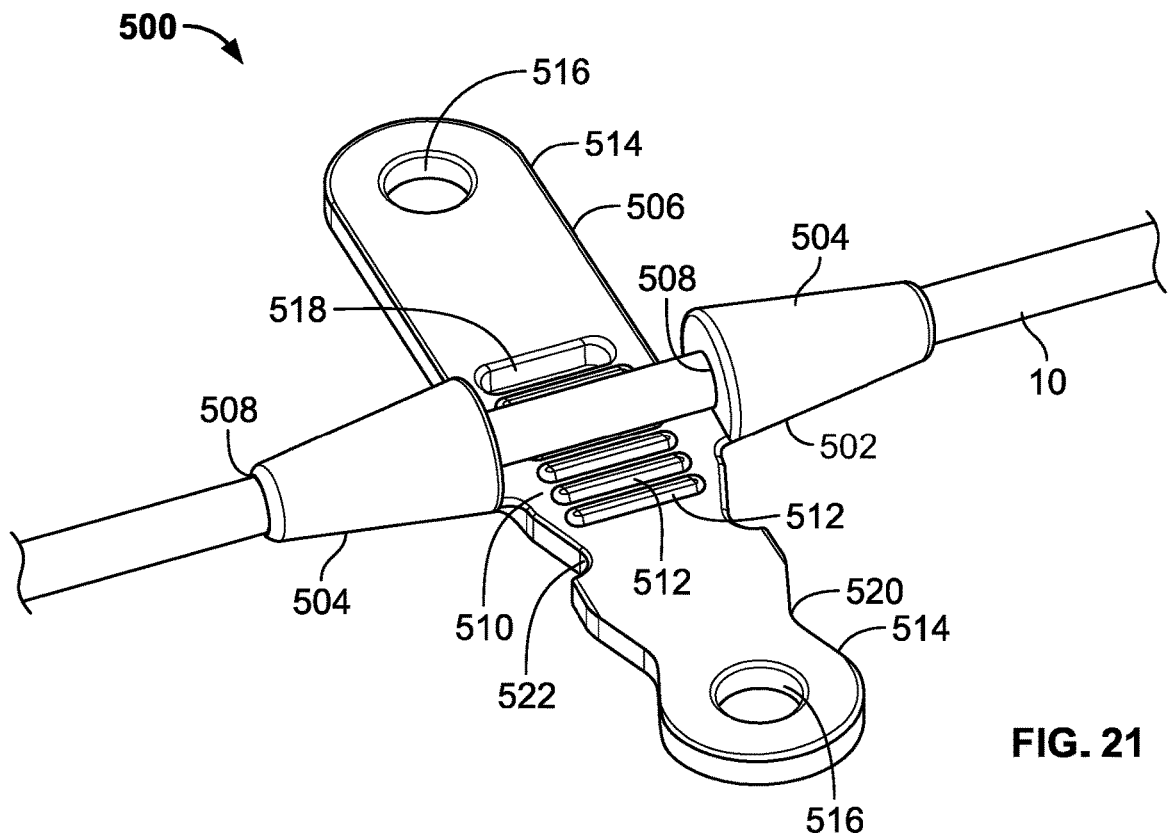
FIG. 21 is a perspective view of a fifteenth example fixation device for a catheter in accordance with various embodiments.
Figure 22:
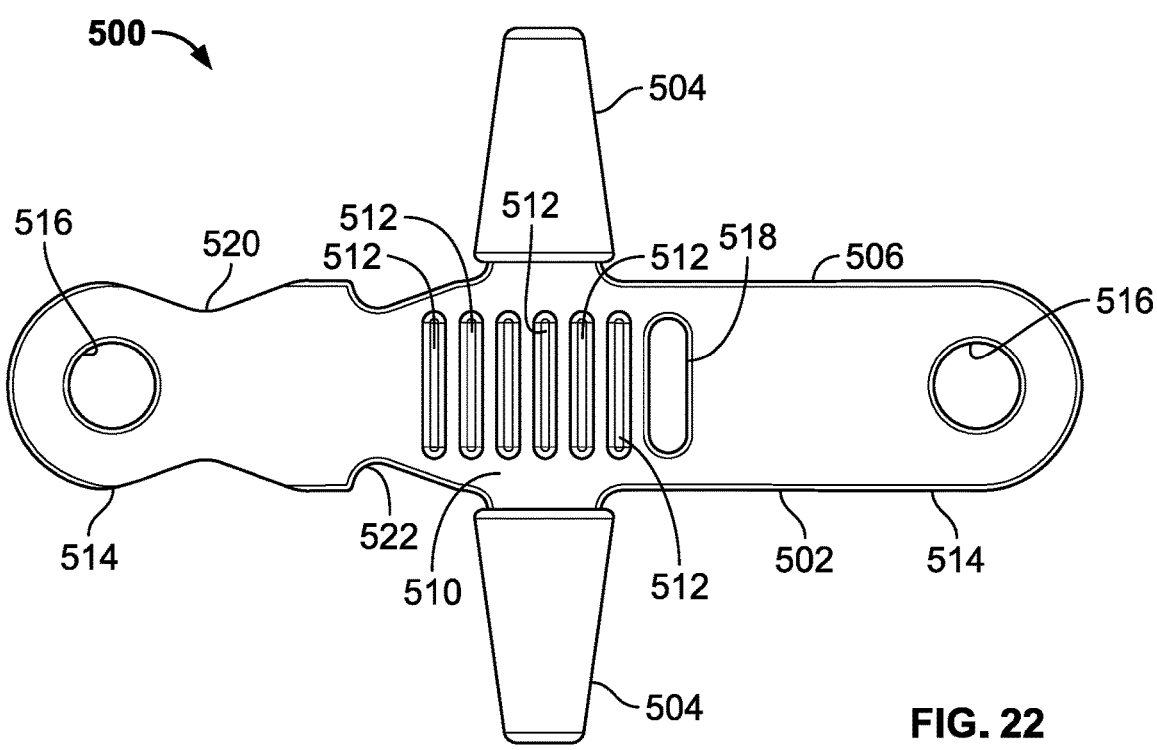
FIG. 22 is a top plan view of the fixation device of FIG. 21.

Another example fixation device 500 is shown in FIGS. 21 and 22. The fixation device 500 of this form includes a body 502 having catheter reception portions 504 spaced apart by and opposing one another over a transverse band 506. In the illustrated form, the catheter reception portions 504 have outwardly oriented frusto-conical shapes with central bores 508 extending longitudinally therethrough. Of course, other shapes can alternatively be utilized. The configuration of the device 500 allows the device to lie flat when implanted.

As shown, the band 506 includes a central portion 510 disposed between the catheter reception portions 504 that includes upwardly protruding ribs 512 or other textured surfaces to engage a catheter. The ribs 512 extend in a longitudinal direction and are spaced transversely from one another. The band 506 further includes tabs or wings 514 that project laterally outwardly from the central portion 510. Each of the tabs 514 includes an opening 516 extending therethrough for reception of a suture to fix the device 500 to tissue.

To tighten the device 500 around a catheter, one of the tabs 514 is a female tab with a slot opening 518 extending therethrough and the other of the tabs 514 is a male tab including first and second waisted portions or notches 520, 522. One or more than two notches can alternatively be utilized. As shown, the slot opening 518 of the female tab 514 has a length generally equal to or slightly larger than the notches 520, 522 of the male tab 514, but smaller than a width of the remaining portions of the male tab 514. With this configuration, a user can bend the tabs 514 toward one another over the central portion 510 and resiliently deform the slot opening 518 and/or male tab 514 until the first notch 520 is received within the slot opening 518. Thereafter, when a user desires to secure the catheter within the device 500, the user can pull on the male tab 514 until the second notch 522 is received within the slot opening 518. As the tabs 514 are tightened together the ribs 512 engage the catheter around a circumference thereof to prevent the catheter from migrating without the use of a suture. As with the above forms, one of the reception portions 504 can be utilized as a plug to seal with the dura in the opening therethrough to prevent CSF leakage. Of course, it will be understood that the device 500 could be provided without the catheter reception portions 504, leaving the band 506. In one form, the body 502 can be composed of silicone 50A.

Figure 23:
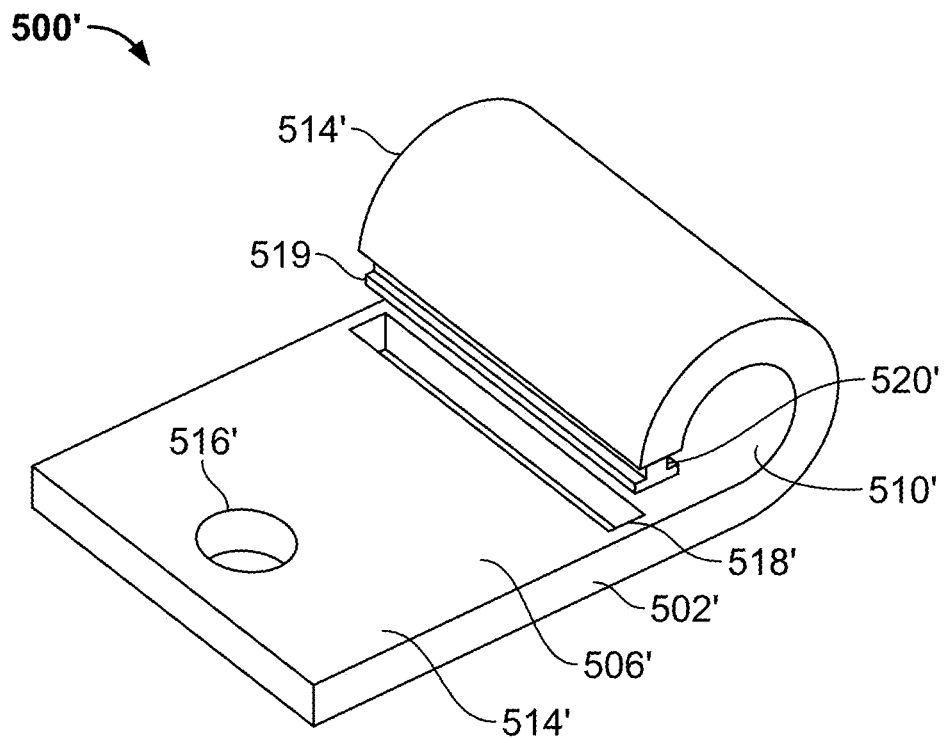
FIG. 23 is a perspective view of a sixteenth example fixation device for a catheter in accordance with various embodiments.
Figure 24:
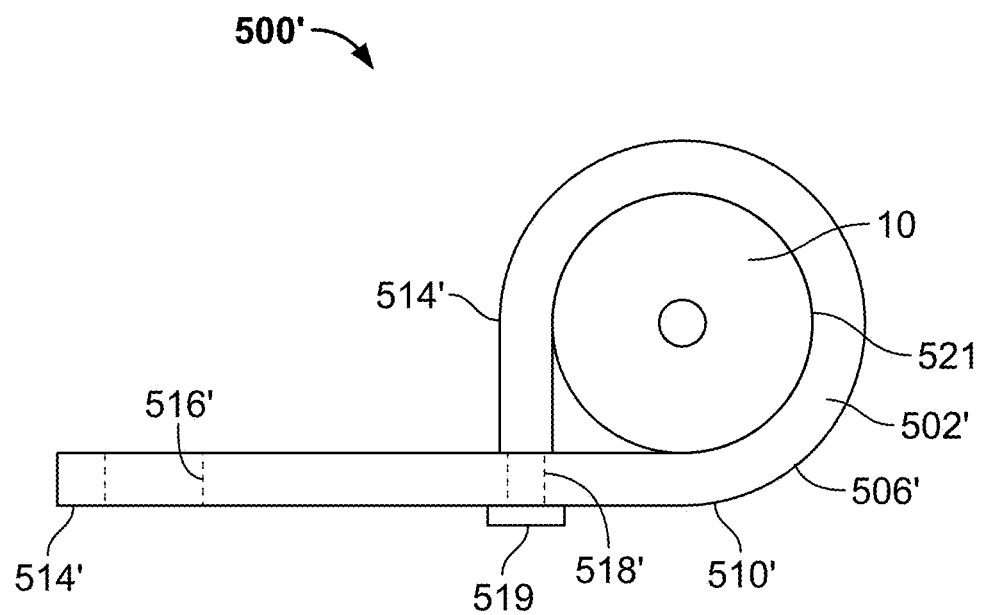
FIG. 24 is a side elevational view of the fixation device of FIG. 23 in a closed configuration.

In one example shown in FIGS. 23 and 24, a fixation device 500' can include a body 502' without the catheter reception portions 504. In this form, the body 502' is a transverse band 506' with at least one end or wing 514' having an opening 516' extending therethrough for reception of a suture to fix the device 500' to tissue. To tighten the device 500' around a catheter, one of the ends 514' is a female tab with a slot opening 518' extending therethrough and the other of the ends 514' is a male tab including a plug 519 with a waisted portion 520'. As shown, the slot opening 518' of the female tab 514' has a length generally equal to or slightly larger than the waisted portion 520' of the male tab 514', but smaller than a width of the remaining portion of the plug 519.

By one approach, the body 502' can be flexible. With this configuration, a user can bend the ends 514' toward one another over a central portion 510' of the band 506' and resiliently deform the slot opening 518' and/or plug 519 until the waisted portion 520' is received within the slot opening 518'. If desired, the body 502' can include ribs configured similarly to the above form, to engage the catheter 10 around a circumference thereof to prevent the catheter 10 from migrating without the use of a suture. By another approach, the body 502' can be rigid with a looped configuration as shown where the male end 514' is spaced from the slot opening 518' and the body 502' defines a bore 521 to receive the catheter 10 therethrough. With this configuration, a user can insert the catheter 10 through the bore 521, position the device 500' at a desired point along the catheter 10, and resiliently flex the body 502 to insert the plug 519 into the slot opening 518'. The plug 521 can be configured to snap-fit within the opening 518' to hold the ends 514' together with the body 502' compressed around an entire perimeter of the catheter 10.

Figure 25:
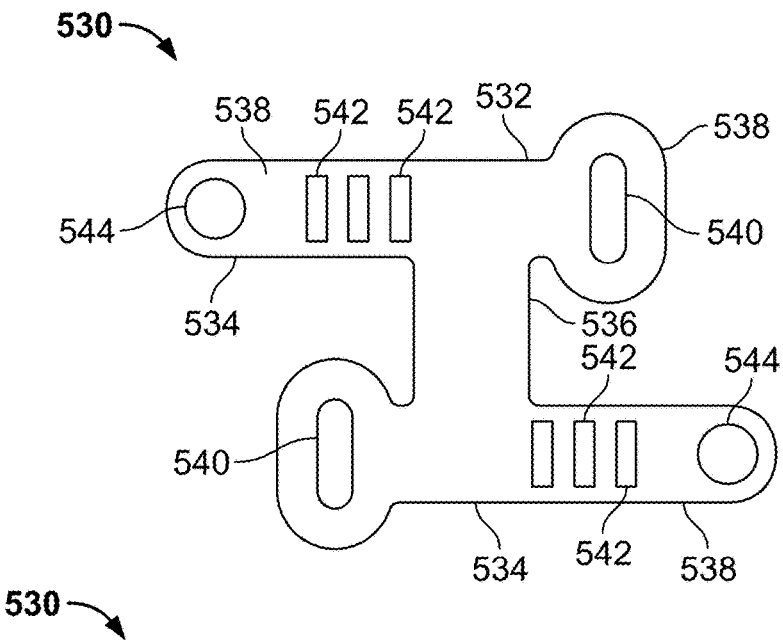
FIG. 25 is a top plan view of a seventeenth example fixation device for a catheter in accordance with various embodiments.
Figure 26:
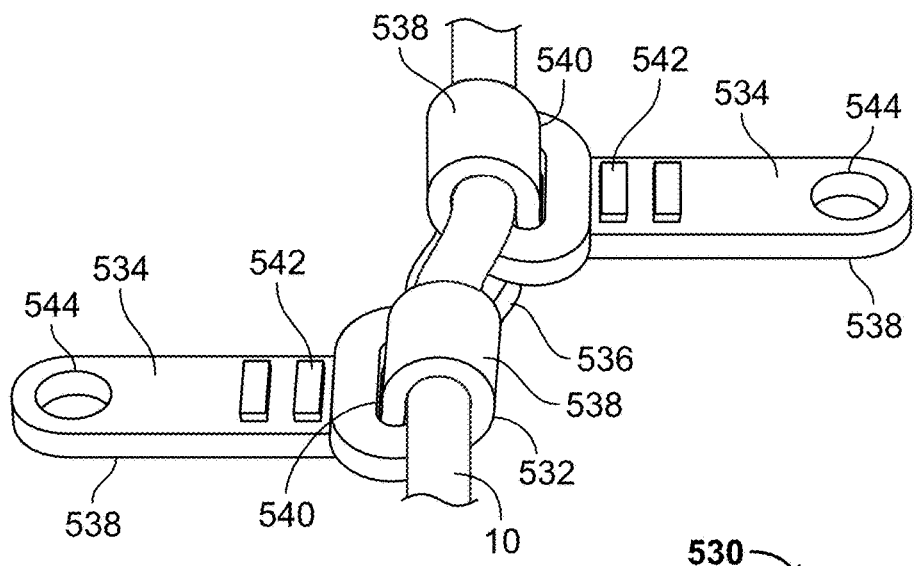
FIG. 26 is a top plan view of the fixation device of FIG. 25 in a closed configuration.
Figure 27:
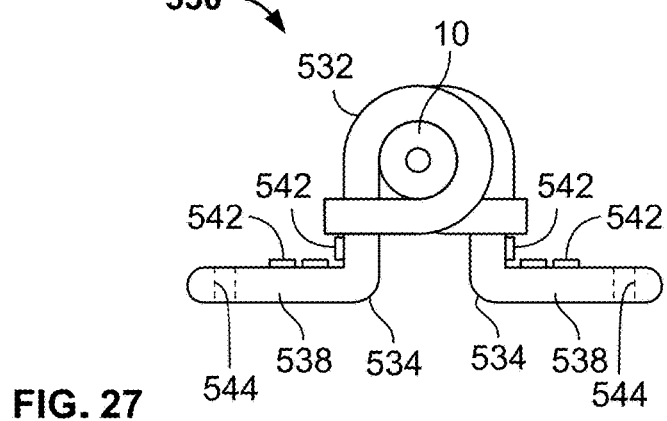
FIG. 27 side elevational view of the fixation device of FIG. 25 in a closed configuration.

In yet another example shown in FIGS. 25 to 27, a fixation device 530 similar to the above forms can include a body 532 without the catheter reception portions 504. In this form, the body 532 includes a pair of stacked transverse bands 534 connected to one another by a central strip 536. Each band 534 includes tabs 538 that project laterally outwardly from the central strip 536. To tighten the bands 534 around a catheter, one of the tabs 538 is a female tab with a slot opening 540 extending therethrough and the other of the tabs 538 is a male tab including a retention portion 542. By one approach, the retention portion 542 can be a plurality of ribs as shown that project upwardly from the male tab 538. As shown, the slot opening 540 of the female tab 538 has a length generally equal to or slightly larger than the male tab 538 and a height generally equal to or slightly larger than the male tab 538. With this configuration, a user can bend the tabs 538 of each of the bands 534 toward one another over the central strip 536 and resiliently deform the slot opening 540 and/or male tab 538 until one of the ribs 542 are forced through the slot opening 540. The rib 542 engages the female tab 538 and holds the respective band 534 in a looped configuration. Thereafter, when a user desires to secure the catheter 10 within the device 530, the user can pull on the male tab 538 until a subsequent rib 542 is received through the slot opening 540. As the tabs 538 are tightened together the body 532 is wrapped around the catheter 10 around a circumference thereof to prevent the catheter from migrating without the use of a suture. By another approach, the retention portion 542 can include first and second waisted portions or notches similar to the above form. If desired, the central strip 536 can include ribs similar to the above form.

As shown, the bands 534 can be disposed in flipped relation to one another such that the male tabs 538 are disposed on opposite sides of the central strip 536. Advantageously, this configuration can be utilized to apply opposing forces on the catheter 10 when the device 530 is tightened thereto and sutured to tissue through openings 544 extending through ends of the male tabs 538. These opposing forces and the resulting tortuous S-shaped path, along with the compression of the bands 534, hold the catheter 10 in a desired location.

Another example fixation device 550 is shown in FIGS. 28 to 31. The fixation device 550 of this form includes a body 552 having catheter reception portions 554 spaced apart by and opposing one another over a transverse band 556. In the illustrated form, the catheter reception portions 554 have outwardly oriented frusto-conical shapes with central bores 558 extending longitudinally therethrough. As shown, in FIG. 29, the catheter reception portions 554 can further include retention structures 559 that extend radially inward into the central bores 558 to thereby engage and grip a catheter inserted therethrough. In the illustrated form, the retention structures 559 extend in an annular configuration around the bore 558 and have a triangular cross-section in a plane extending longitudinally with the bore 558. Of course, other shapes for the catheter reception portions 554 and the retention structures 559 can alternatively be utilized. Advantageously, the retention structures 559 can be sized to tightly engage a catheter inserted through the catheter reception portions 554 to thereby prevent fluid flow, such as CSF, through the catheter retention portions 554.

The configuration of the device 550 allows the body 552 to lie generally flat when implanted. As shown, the band 556 includes a central portion 560 disposed between the catheter reception portions 554 that includes upwardly protruding ribs 562 or other textured surfaces. The ribs 562 extend in a direction generally parallel with longitudinal axes of the bores 558 and are spaced transversely from one another along the central portion 560. The band 556 further includes tabs 564 that project laterally outwardly from the central portion 560. Each of the tabs 564 includes an opening 566 extending through and end portion thereof for reception of a suture to fix the device 550 to tissue.

To tighten the device 550 around a catheter, one of the tabs 564 is a female tab 564a with a slot opening 568 extending therethrough and the other of the tabs 564 is a male tab 564b including a notch 570 and an elongate neck portion 572. Two or more notches can alternatively be utilized. As shown, the slot opening 568 of the female tab 564a has a length generally equal to or slightly larger than the notch 570 and the neck portion 572 of the male tab 564b, but smaller than a width of the remaining portions of the male tab 564b. Further, the neck portion 572 can have a smaller width than the notch 570 so that it can be easily inserted through the slot opening 568. As shown, the central portion 560 can have notches 574 on either side thereof on a side of the band 556 with the male tab 564b. The notches 574 extend to align with an edge of the bores 558, which allows the male tab 564b to be flexed along a portion disposed adjacent to the bores 558.

With this configuration, a user can insert a catheter through the catheter reception portions 554 until the body 552 is positioned at a desired location along the catheter. Thereafter, the user can bend the tabs 564 toward one another over the central portion 560 and the catheter so that the ribs 562 are distributed about a circumference of the catheter. The user can then resiliently deform the slot opening 568 and/or male tab 564b and insert the male tab 564b through the slot opening 568 until the notch 570 is received within the slot opening 568. The device 550 can be sized and configured so that with the notch 570 engaged with the slot opening 568, the ribs 562 tightly engage the catheter to thereby retain the body 552 on the catheter and prevent the catheter from migrating without the use of a suture. As with the above forms, one of the reception portions 554 can be utilized as a plug to seal with the dura in the opening therethrough to prevent CSF leakage. This is further enhanced by the retention structure 559 preventing fluid flow through the catheter retention portions 554. In one form, the body 552 can be composed of silicone 50A.

In one example form, the band 556 can have a length of about 0.89 inches and a thickness of about 0.06 inches; the suture openings 566 can have a diameter of about 0.07 inches; the bores 558 can have an inner diameter of about 0.05 inches and the retention portions 554 can extend to an inner diameter within the bores 558 of about 0.035 inches; the bores 558 and central portion 560 can have a combined width of about 0.58 inches; and the notches 574 can have a width of about 0.02 inches. The body 552 can be made from silicone, such as silicone med-4850, or other suitable materials.

Another example fixation device 600 is shown in FIGS. 32 to 35. The device 600 includes a body 602 having tapered ends 604, such that the ends 604 can be utilized as a plug to seal with the dura in the opening therethrough. The body 602 includes a central bore 606 extending longitudinally therethrough. As shown in the figures, the bore 606 can include inwardly projecting ribs, rings, or other textured surfaces 608 that maximize a catheter engagement surface area and grip with the catheter. It will be understood that the catheter engagement surfaces of any of the embodiments described herein can include similar textured surfaces to maximize a catheter engagement surface area and grip. In one form, the interior diameter of the central bore 606 can be sized smaller than an outer diameter of the catheter so that the body 602 tightly engages the catheter. The body 602 can be composed of a low durometer silicone.

Figure 32:
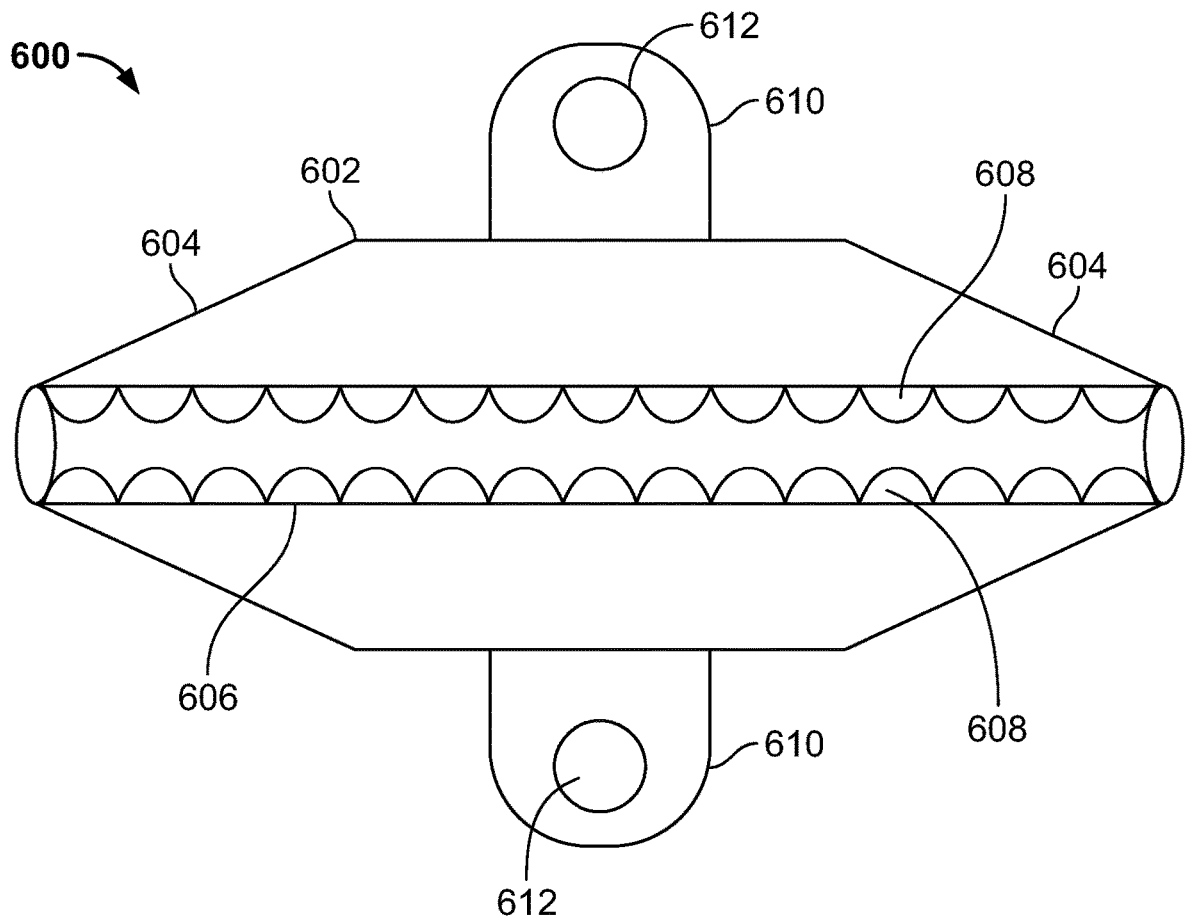
FIG. 32 is a cross-sectional view of a nineteenth example fixation device for a catheter in accordance with various embodiments.
Figure 33:
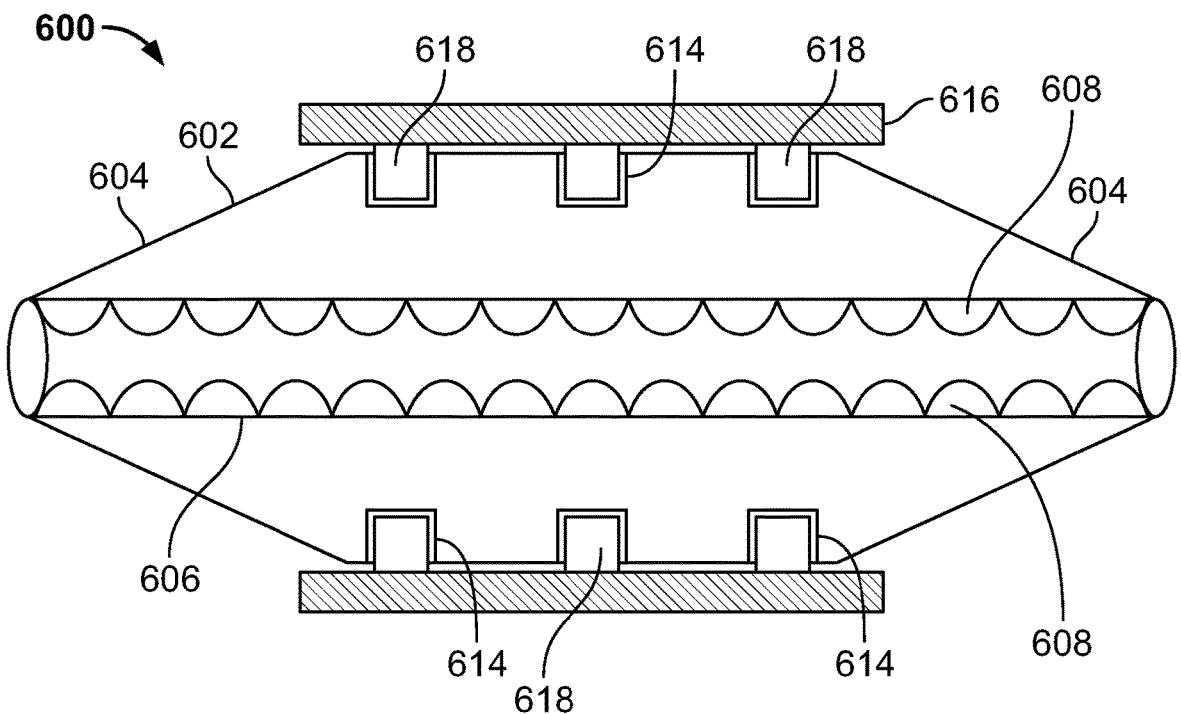
FIG. 33 is a cross-sectional view of a twentieth example fixation device for a catheter in accordance with various embodiments.
Figure 34:
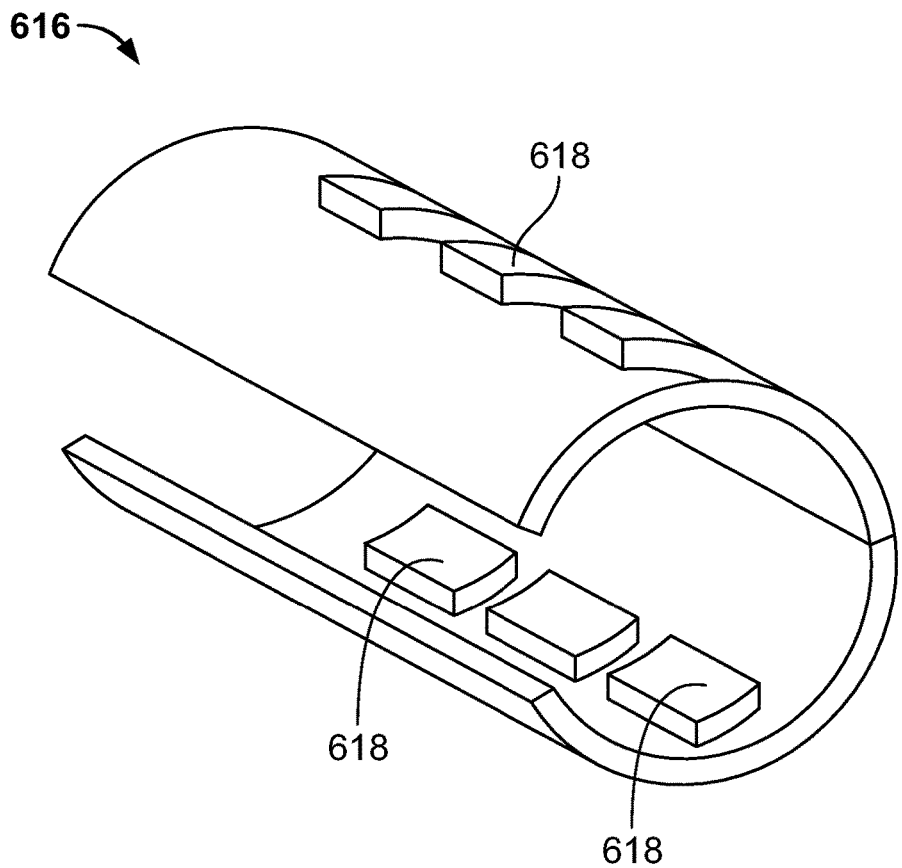
FIG. 34 is a perspective view of a clamping member for the fixation device of FIG. 33.
Figure 35:
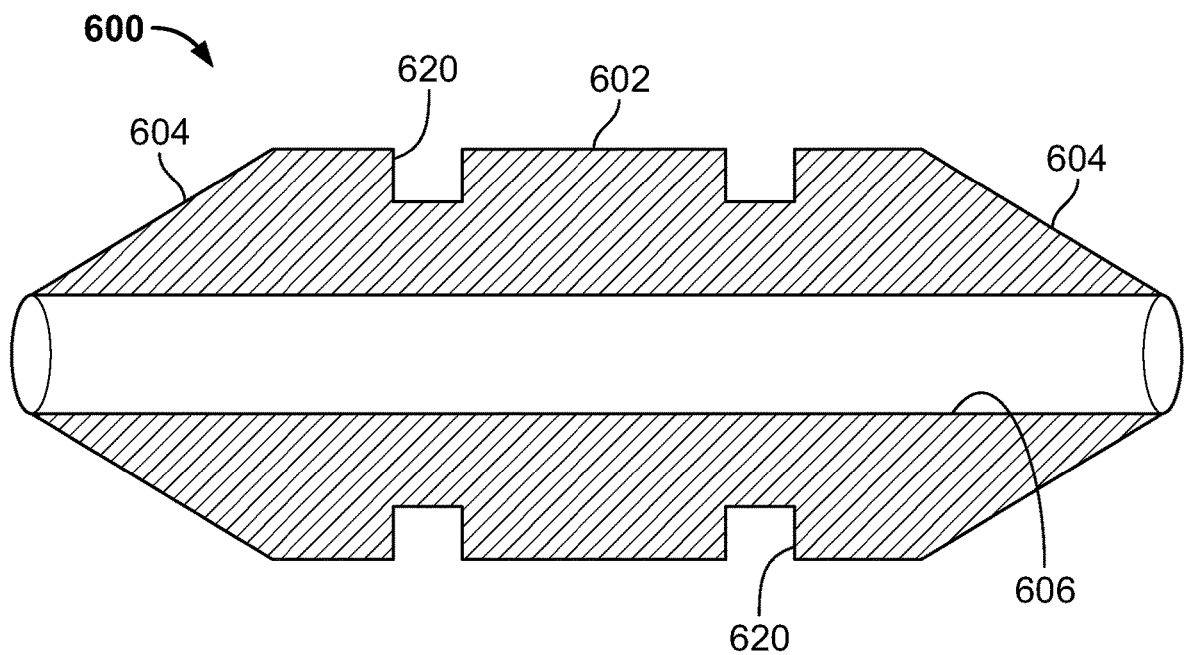
FIG. 35 is a cross-sectional view of a twenty first example fixation device for a catheter in accordance with various embodiments.

In a first form shown in FIG. 32, the body 602 can include outwardly extending tabs 610 having openings 612 extending therethrough. So configured, a user can suture the device 600 in place using the openings 612 to prevent the catheter 10 from migrating. In a second form shown in FIGS. 33 and 34, the body 602 can include grooves or annular channels 614 extending therearound and the device 600 can further include a clamp 616 having grip portions or protrusions 618 configured to be inserted into the grooves 614 to orient the clamp 616 on the body 502 and prevent slippage therebetween. The clamp 616 can be secured over the body 602 to apply compressive pressure on the body 602 and the catheter received within the body 602. The clamp 616 can have a clam-shell configuration, for example. The device 600 of this form can be sutured in place, such as through the openings 612 in the tabs 610, around portions of the clamp 616 and/or body 602, or combinations thereof. In an alternative form shown in FIG. 35, the body 602 can include grooves or annular channels 620 extending therearound to receive sutures. The grooves 620 help the sutures stay in place around the body 602 and can be used to compress the body 602 to tighten on the catheter therein.

Another example fixation device 700 is shown in FIGS. 36 to 40. The fixation device 700 of this form includes an elongate main body 702 having a tubular configuration with a proximal end 704 and a distal end 706. The body 702 has an outwardly bulging intermediate or central portion 708 and has a tapered profile extending from the central portion 708 to the proximal and distal ends 704, 706. The conical profile of the ends 704, 706 can advantageously be utilized to act as a plug when a user inserts the respective end 704, 706 into the opening through the dura of a patient. The inwardly tapered profile of the end 704, 706 seals with the dura in the opening therethrough to prevent or minimize the leakage of CSF. If desired, the body 702 can be symmetrical so that the proximal and distal ends 704, 706 have similarly tapered profiles and can each be used as a plug. This allows a user to implant the device 700 without having to worry about orientation.

Figure 40:
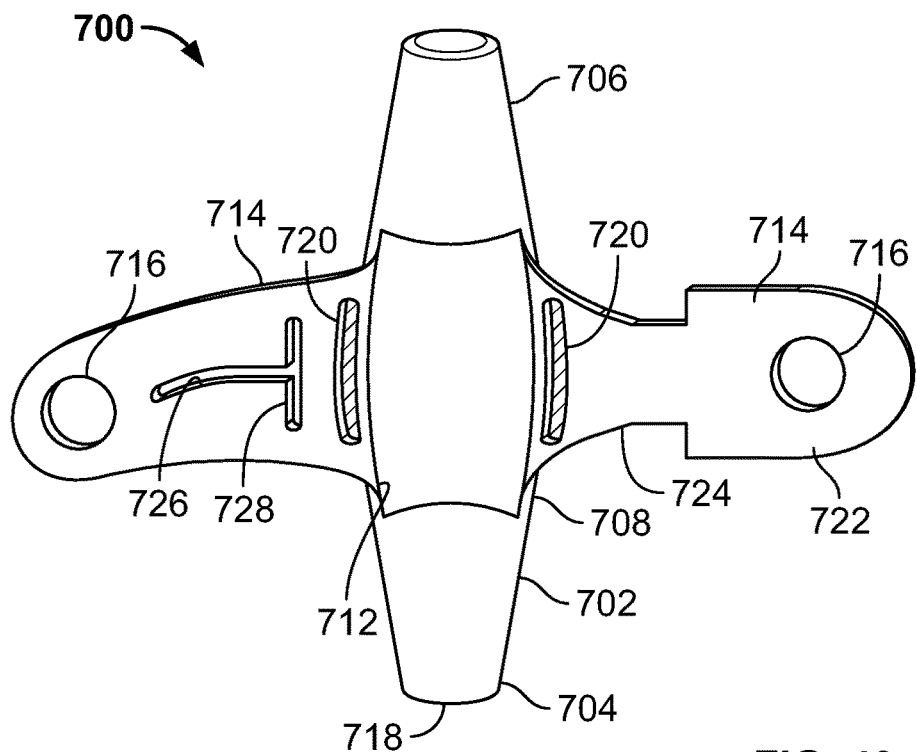
FIG. 40 is a top plan view of the fixation device of FIG. 36 in an open configuration.
Figure 41:
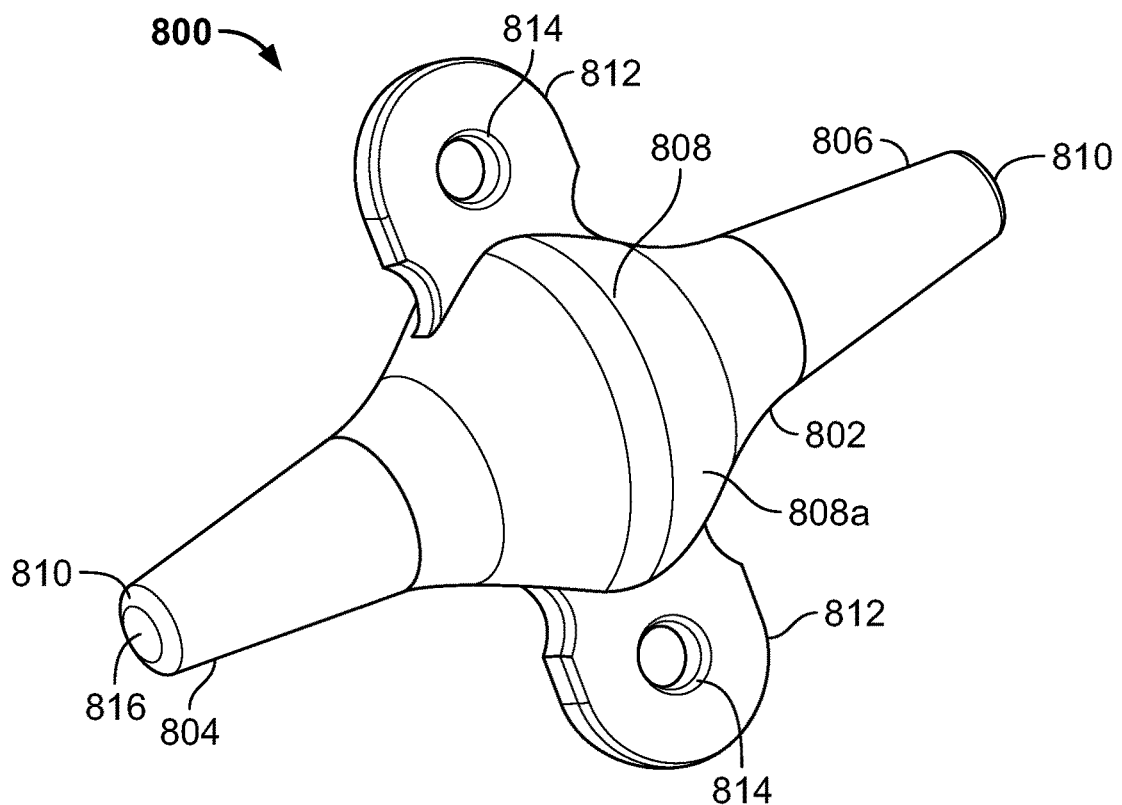
FIG. 41 is a perspective view of an twenty third example fixation device for a catheter in accordance with various embodiments.

As shown in FIG. 40, the body 702 includes a radially-oriented central opening 712 in the central portion 708 with wings 714 extending laterally outward from edges of the opening 712. Each of the wings 714 includes an opening 716 extending therethrough so that a user can suture the device 700 in place using the openings 716 to prevent the catheter 10 from migrating. The central opening 712 extends along a longitudinal length of the body 702 exposing a central bore 718 that runs therethrough. In some versions, the one or both of the wings 714 can include teeth, ribs, or other textured surfaces 720 extending adjacent to the central opening 712 to grip a catheter 10 inserted within the bore 718.

Figure 38:
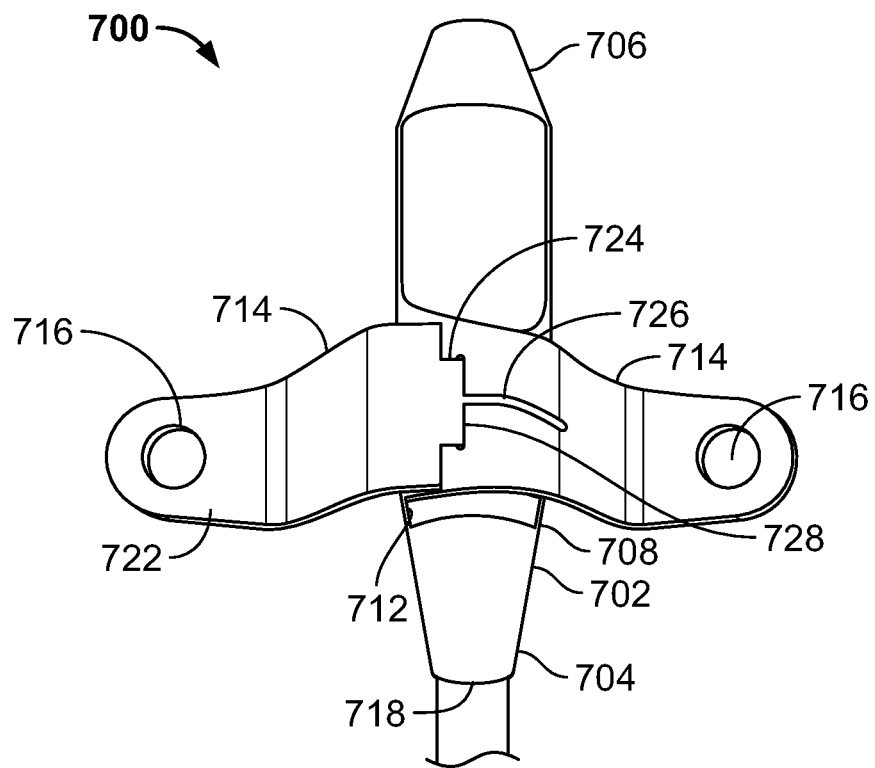
FIG. 38 is a top plan view of the fixation device of FIG. 36 having a distal tip in a bent configuration.
Figure 39:
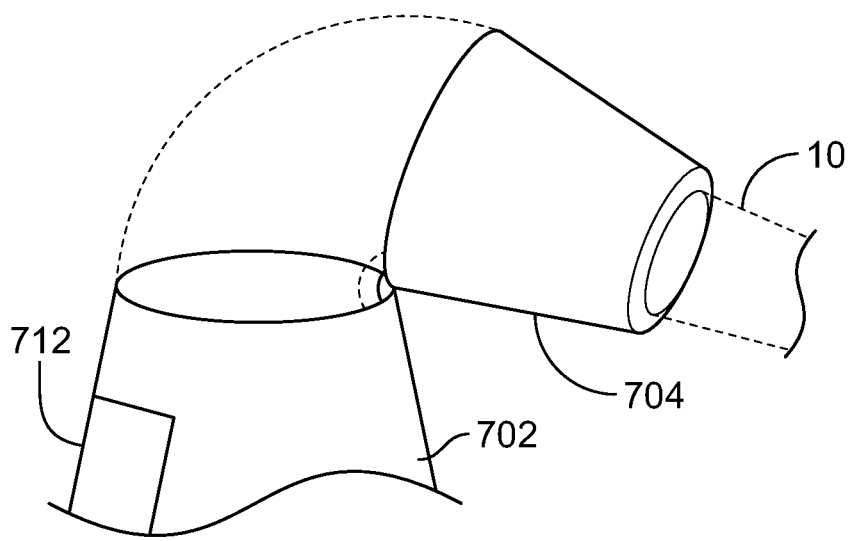
FIG. 39 is a sectional view of the fixation device of FIG. 36 having a distal tip in a bent configuration.

In some versions, one or both of the ends 704, 706 can be bendable with respect to horizontal and the remaining portion of the body 702 so that the end 704, 706 can be inserted into the dura opening while the remaining portion of the body 702 extends along or lies flat against the fascia. As shown in FIGS. 38 and 39, the opening 712 can be sized to allow the adjacent end 704, 706 to bend and the body 702 can be composed of a flexible material as described herein.

As shown in FIG. 40, the wings 714 include a male wing and a female wing. The male wing 714 includes an outer tab portion 722 and a waisted portion or notch 724, while the female wing 714 includes a laterally disposed slot 726 having a first length that extends away from the body 702 and a longitudinally disposed slot 728 having a second length that extends generally parallel with the body 702 adjacent to the central opening 712 at a base of the female wing 714. The first length corresponds to a largest width of the male wing 714, while the second length corresponds to the narrowest width, i.e., the notch 724, of the male wing 714. So configured, the male wing 714 can be twisted so that the tab portion 722 aligns with the lateral slot 726 and pulled therethrough. Thereafter, when a user desires to secure the catheter 10 in place, the male wing 714 can be pulled through the lateral slot 726 until the notch 724 aligns with the longitudinal slot 728 and twisted so that the notch 724 of the male wing 714 rests within the longitudinal slot 728.

Figure 36:
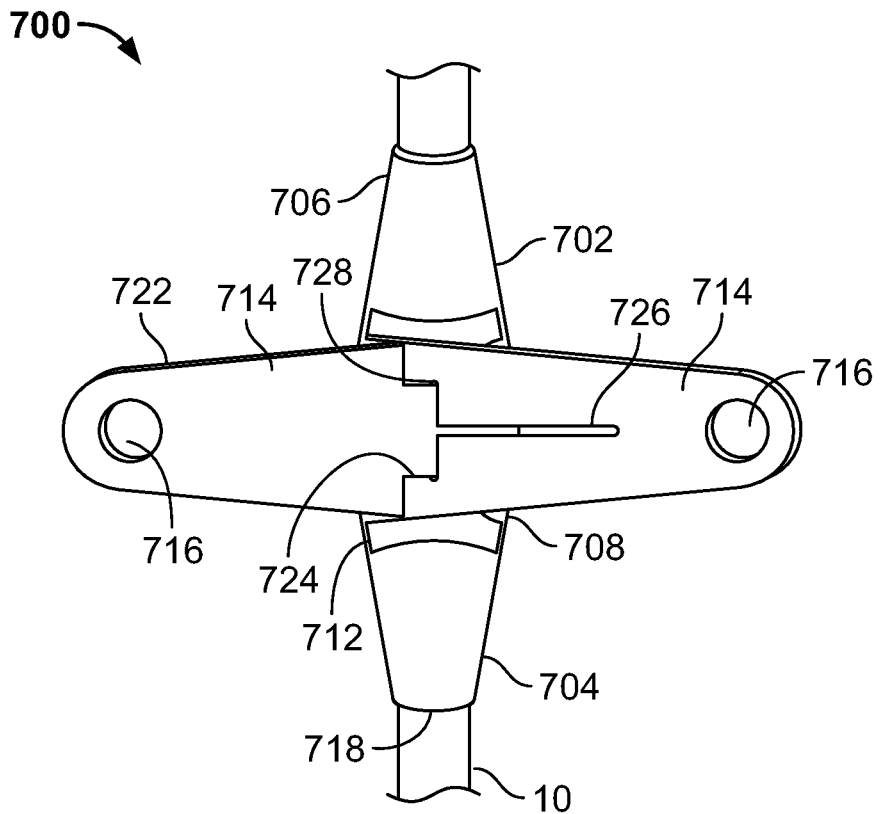
FIG. 36 is a top plan view of a twenty second example fixation device for a catheter in accordance with various embodiments.
Figure 37:
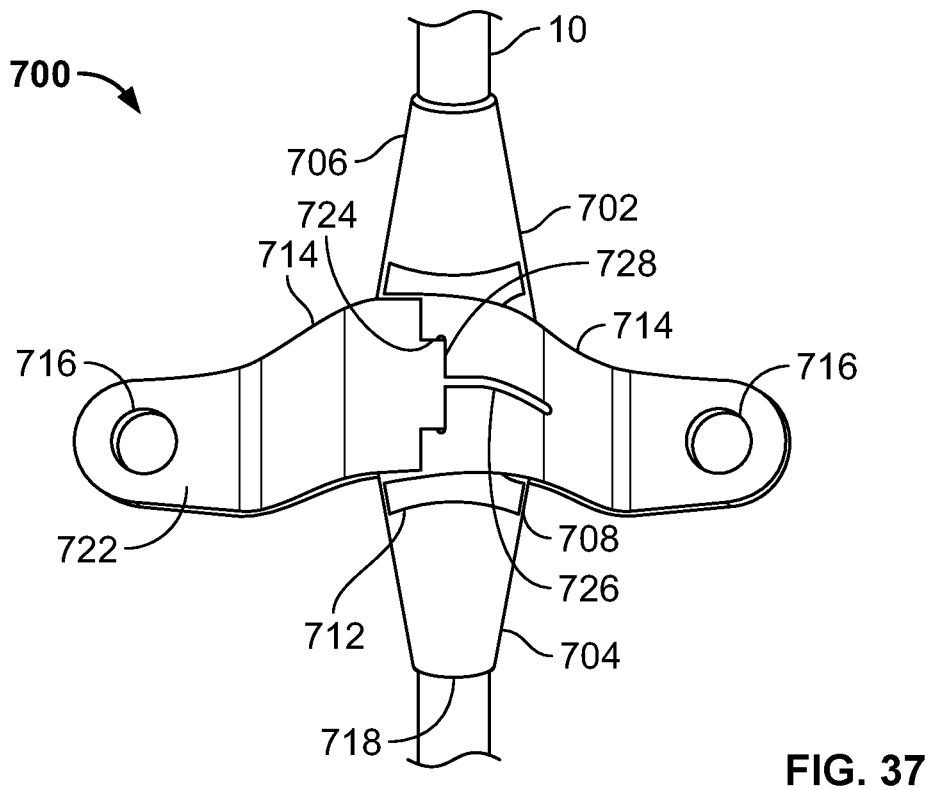
FIG. 37 is a top plan view of the fixation device of FIG. 36 having suture tabs in a bent configuration.

The fixation device 700 can be provided to a user already partially assembled, with the male wing 714 twisted and partially inserted through the lateral slot 726. The user can then easily slide the fixation device 700 onto the catheter 10 with no or minimal resistance or drag. Once the fixation device 700 is in the desired position, the male wing 714 can be pulled fully through the female wing 714 until the male wing 714 reaches the secured position (FIG. 36). The user can then suture the wings 714 to the fascia or other tissue using the suture openings 716. If the fixture device 700 is being used at the dura, one of the ends 704, 706 can be bent (FIGS. 38 and 39) so that the body 702 lies flat against the fascia. The wings 714 can come with a slight bend already built into the design for easier anchoring (FIG. 37). The advantage of this design is that the wings 714 do not need to be in any specific orientation after being secured together to still secure the catheter 10 within the device 700. Further, the fixation device 700 does not have to rely on sutures for securing onto the catheter 10, as the disassembly process would be difficult if not impossible to do accidentally.

Another example fixation device 800 is shown in FIGS. 41 to 44. The fixation device 800 of this form includes an elongate body 802 with a proximal end 804 and a distal end 806. The body 802 has an outwardly bulging intermediate or central portion 808. In a first form shown in FIG. 41, the bulging portion 808 has a single, central bulbous portion 808a with a smooth curved profile. In a second form shown in FIG. 43, the bulging portion 808 includes a central bulbous portion 808a and rings 808b disposed on either side of the central portion 808a giving the body 802 an undulating profile. In both forms, the body 802 can have a tapered profile transitioning from the bulging portion 808 to the proximal and distal ends 804, 806. The tapered profile of the body 802 at the ends 804, 806 thereof can advantageously be utilized to act as a plug when a user inserts one of the ends 804, 806 into the opening through the dura of a patient. The inwardly tapered profile of the ends 804, 806 acts to seal with the dura in the opening therethrough to prevent or minimize the leakage of CSF. As shown, the tapered ends 804, 806 taper downwardly so that tips 810 thereof are slightly, e.g., between about 1 mm to 3 mm, larger than an outer diameter of the catheter 10 due to a wall thickness of the body 802. If desired, the body 802 can be symmetrical so that the proximal and distal ends 804, 806 have similarly tapered profiles and can each be used as a plug. This allows a user to implant the device 800 without having to worry about orientation.

As shown in the figures, the body 802 can also include outwardly extending tabs 812 having openings 814 extending therethrough that allow for easy placement of sutures to secure the fixation device 800 and catheter 10 to surrounding tissue. Two tabs 812 can be centrally located along the body 402, as shown, but other configurations and numbers are possible.

Figure 42:
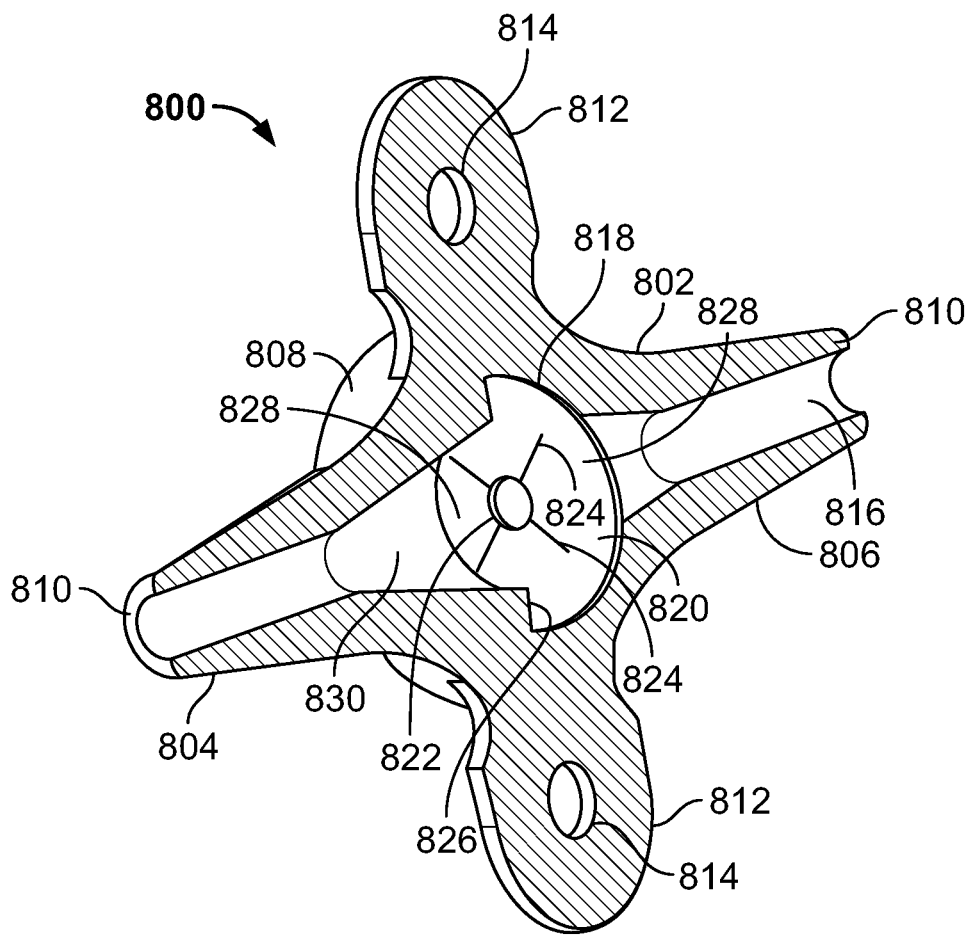
FIG. 42 is a cross-sectional view of the fixation device of FIG. 41.
Figure 43:
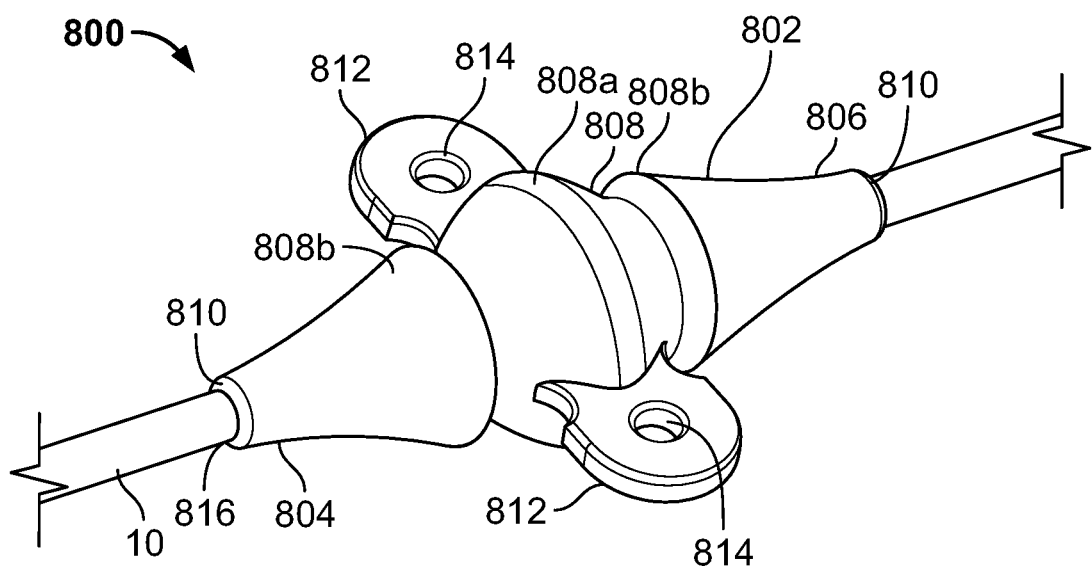
FIG. 43 is a perspective view of a twenty fourth example fixation device for a catheter in accordance with various embodiments.
Figure 44:
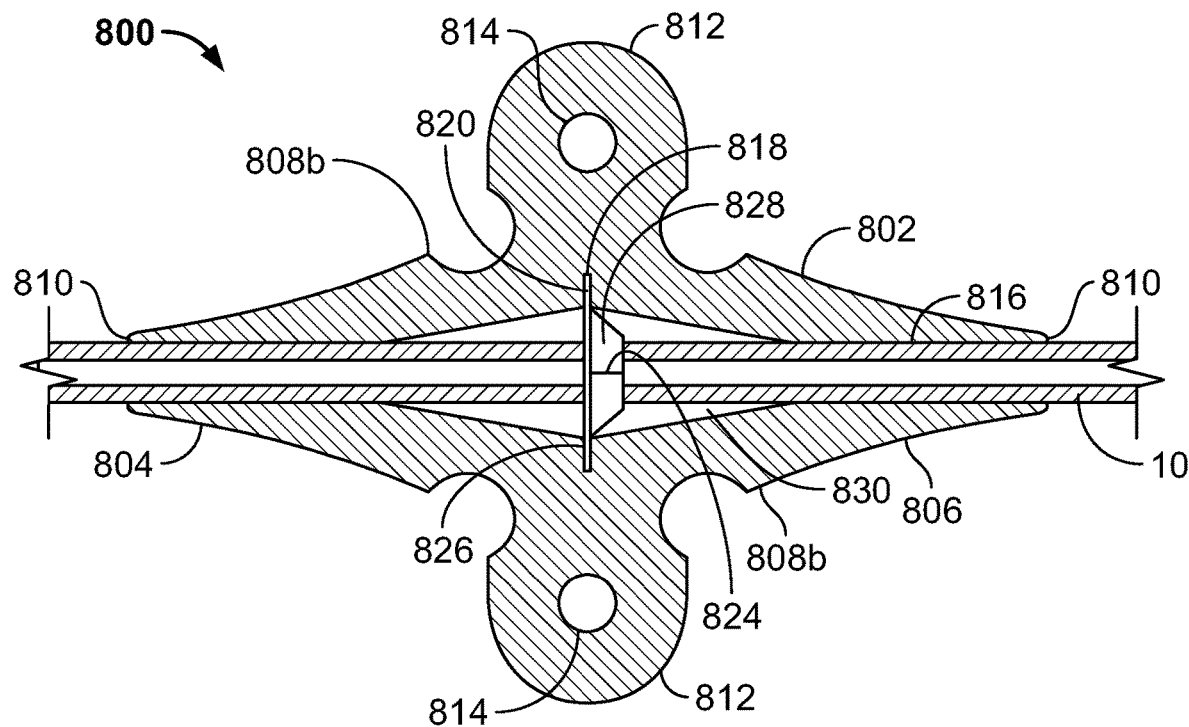
FIG. 44 is a cross-sectional view of the fixation device of FIG. 43.

Turning now to FIGS. 42 and 44, the body 802 includes a central bore 816 extending longitudinally therethrough along the longitudinal axis L that is sized to receive a catheter 10. While the device 800 may be suitable for many purposes in this form, the device 800 can further include one or more toggle or one-way valves 818 extending across the inner diameter of the central bore 816. The valves 818 are configured to allow the catheter 10 to only move in a single direction therethrough and, thus, through the body 802. Accordingly, the valves 818 allow a user to insert the catheter 10 through the body 802, but thereafter resists or prevents retrograde slippage of the catheter 10 through the device 800. In the illustrated form, the valve 818 has a disc-shaped body 820 with a central aperture 822 and slits 824 extending radially from the central aperture 822. The body 820 can include an annular cavity 826 sized to receive edges of the disc-shaped body 820 therein. With this configuration, a user can insert the catheter 10 through the central aperture 822 of the valve 818. The outer diameter of the catheter 10 is larger than the diameter of the central aperture 822 and, as such, pushing the catheter 10 through the aperture 822 causes wedge portions 828 defined by the slits 824 to deflect or flex and engage the catheter 10. The deflected wedge portions 828 allow the catheter 10 be fed therethrough with a minimal amount of friction, but prevent reverse movement by providing holding strength. As shown, the bore 816 can include an expanded central portion 830 to allow the valve 818 to easily deform when the catheter 10 is inserted therethrough. The diameter of the central aperture 822 controls the amount of flex in the wedge portions 828 and the central aperture 822 can guide the catheter 10 to stay within a center of the bore 816. In some versions, the valve 818 can be configured to toggle in an opposite direction by overcoming the holding strength of the wedge portions 828, which causes the wedge portions 828 to deflect in the opposite direction and thereby reverse the holding strength. The advantage of such a toggle valve 818 is to allow a user to insert the catheter 10 through the fixation device 800 and slide the fixation device 800 to the intended area on the catheter 800. The user would be able to fix the device 800 to the patient without losing adjustability of the catheter's position within the patient or the fixation device 800. The user is able to set the direction of hold with the "toggle" feature, which would allow further insertion of the catheter 10 into the intended area and confidence that the catheter 10 would not back out of the intended final position.

With either of the above versions, after a user has implanted the catheter 10, a user can then advance the fixation device 800 over the catheter 10 to a final desired position. Then, the user can suture the device 800 in place using the openings 814 to prevent the catheter 10 from migrating. The device 800 can be sutured in any desired location, including to the fascia at the site of the dura entry, away from the dura, e.g., Scarpa's fascia, in a port pocket, and so forth. In some versions, body 802 can be composed of silicone and can be molded over the valve 818, which can be composed of PEEK.

Another example fixation device 900 is shown in FIGS. 45 to 49. The fixation device 900 of this form includes a body 902 having proximal and distal ends 904, 906 with a bore 908 extending therethrough. One or both of the ends 904, 906 can have a tapered profile so that the ends 904, 906 can advantageously be utilized to act as a plug when a user inserts one of the ends 904, 906 into the opening through the dura of a patient. The inwardly tapered profile of the ends 904, 906 acts to seal with the dura in the opening therethrough to prevent or minimize the leakage of CSF. As shown, the tapered ends 904, 906 taper downwardly so that tips 910 thereof are slightly, e.g., between about 1 mm to 3 mm, larger than an outer diameter of the catheter 10 due to a wall thickness of the body 902. If desired, the body 902 can be symmetrical so that the proximal and distal ends 904, 906 have similarly tapered profiles and can each be used as a plug. This allows a user to implant the device 900 without having to worry about orientation.

The body 902 further includes an outwardly projecting flange 912 having a plurality of openings 914 extending longitudinally therethrough around a circumference of the flange 912. As with the above forms, the openings 914 can be utilized to secure the device 900 to tissue using one or more sutures. Specifically, after one of the ends 904, 906 is inserted into the dura opening, a user can secure the flange 912 to the fascia using one or more sutures. In one example, a purse-string suture can be used to secure the device 900 to the fascia. In a first form shown in FIG. 45, the flange 912 has a circular shape extending outwardly from the proximal and distal ends 904, 906. In a second form shown in FIG. 47, the flange 912 can include slots 916 that extend radially inwardly from edges thereof. With this form, the flange 912 is divided into wedge portions 918 that can be flexed independently of one another. This configuration advantageously allows the wedge portions 918 of the flange 912 to be folded over the catheter 10 without excessively projecting outwardly from the tissue.

Figure 45:
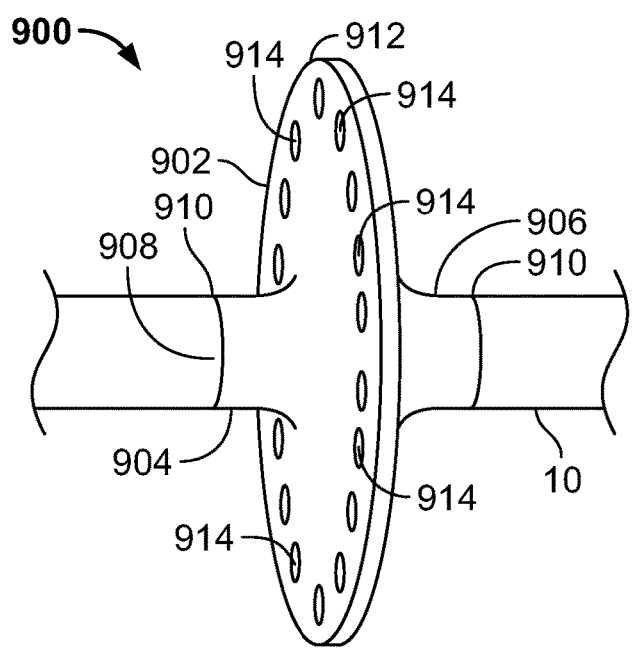
FIG. 45 is a perspective view of a twenty fifth example fixation device for a catheter in accordance with various embodiments.
Figure 46:
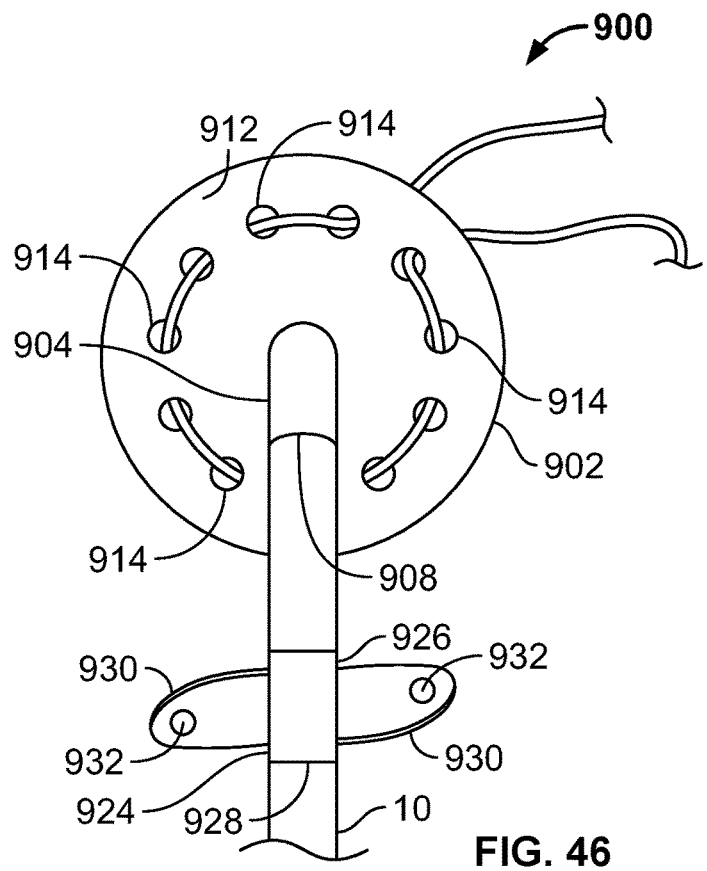
FIG. 46 is a top plan view of the fixation device of FIG. 45.
Figure 47:
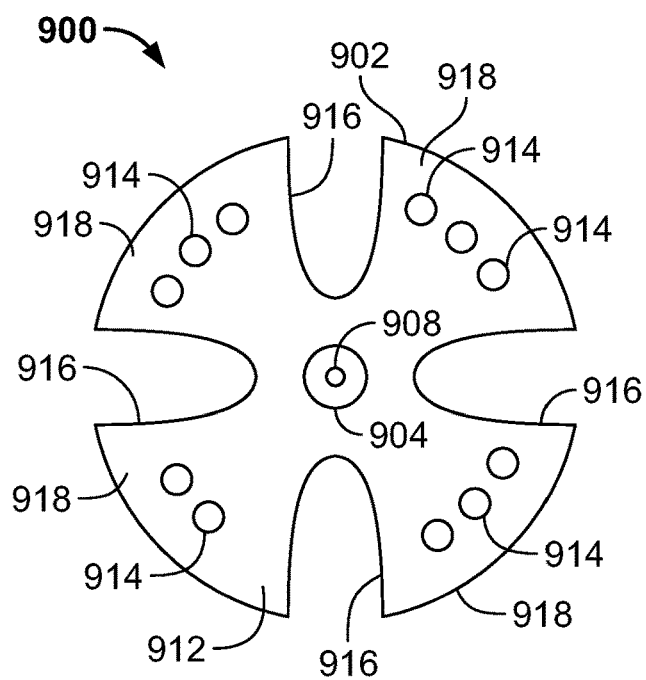
FIG. 47 is a top plan view of an alternative suture disc configuration for the fixation device of FIG. 45.
Figure 48:
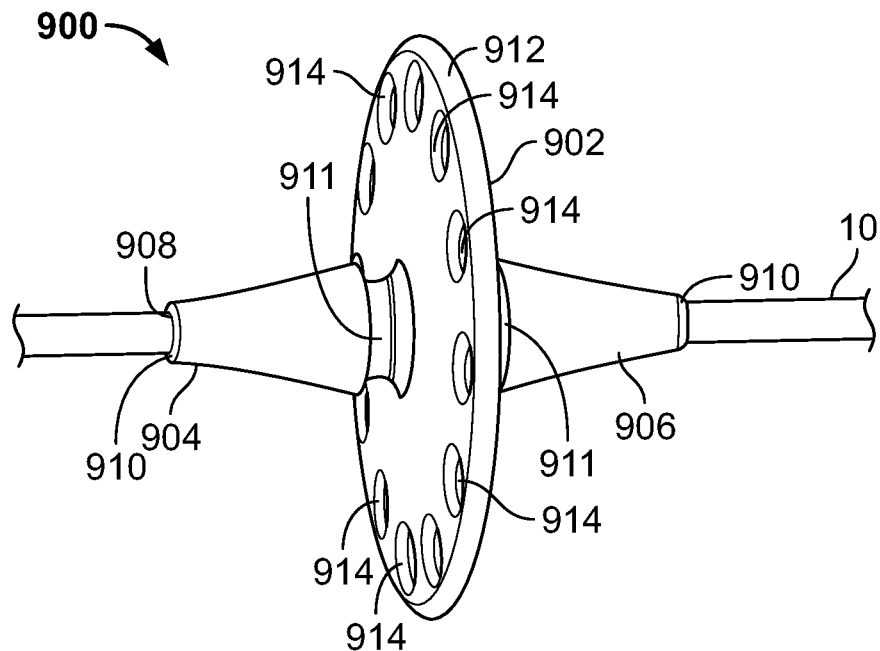
FIG. 48 is a perspective view of a twenty sixth example fixation device for a catheter in accordance with various embodiments.

As shown in FIG. 45, the proximal and distal ends 904, 906 extend away from the flange 912 in a consistent conical shape. In another version, as shown in FIG. 48, the proximal and distal ends 904, 906 can include waisted portions 911 extending therearound adjacent to the flange 912.

Figure 49:
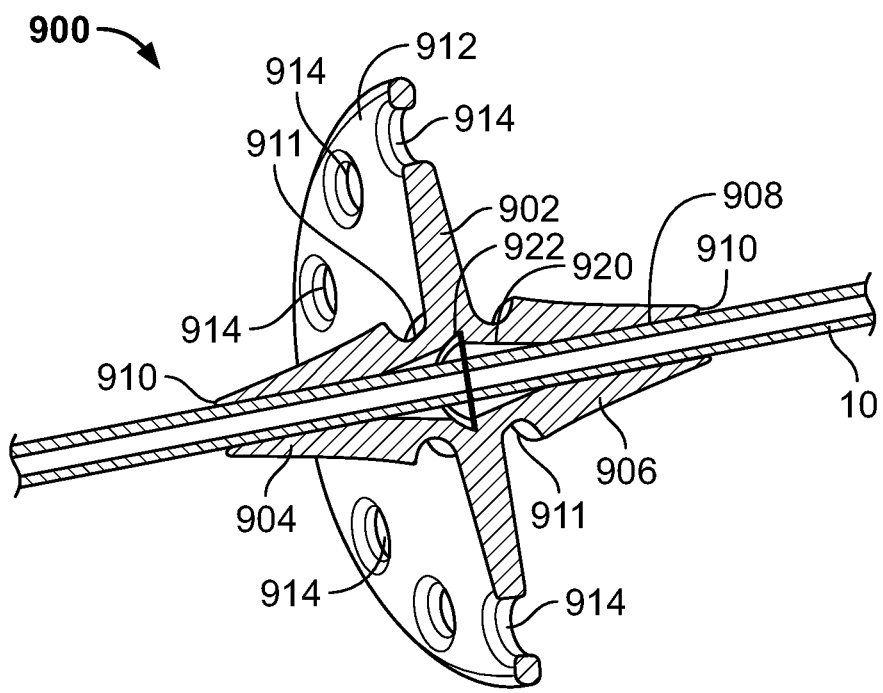
FIG. 49 is a cross-sectional view of the fixation device of FIG. 48.

Turning now to FIG. 49, the central bore 908 can include an expanded central portion 920 and a valve 922 disposed thereacross, similar to the above embodiment of FIG. 44. The valve 922 can be a toggle or one-way valve as previously described and the expanded portion 920 can allow the valve 922 to easily deform when the catheter 10 is inserted therethrough.

The body 902 can advantageously be utilized to plug the dura opening and secure to the fascia therearound. If desired, the fixture device 900 can further include a catheter securing member 924 that fixes the catheter 10 to tissue remote from the dura. The member 924 includes an annular body 926 with a central bore 928 extending therethrough and tabs 930 extending laterally from the body 926. The tabs 930 each include a suture opening 932 extending therethrough. The inner diameter of the annular body 926 can be equal to or slightly smaller than an outer diameter of the catheter 10 to tightly engage the catheter 10 when disposed therearound. The member 924 can be composed of a flexible material, such as silicone as described above, so that the member 924 can be deformed and easily threaded over the catheter 10. The member 924 can be threaded over the catheter 10 to a desired location and secure to the tissue of a patient at a desired location. When used in combination with the body 902, the dura is plugged and the catheter 10 is held against the fascia and prevented from migrating. In some forms, the body 902 can be composed of silicone 50A.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples without departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A fixation device for a catheter, the fixation device comprising:
    an elongate band having a flexible configuration and including a female end having a coupling opening extending therethrough and an opposite, male end;
    a first suture opening extending through the female end;
    a second suture opening extending through the male end; and
    a retention portion of the male end having laterally aligned side notches in opposing edges of the male end to reduce a width of the male end in the retention portion to be equal to or less than a width of the coupling opening of the female end, the coupling opening of the female end configured to receive the retention portion of the male end therein to thereby secure the elongate band around the catheter;
    wherein the elongate band has a flat, first configuration and a second configuration with the retention portion of the male end received within the coupling opening of the female end.

2. The fixation device of claim 1, wherein the elongate band further includes a catheter engagement portion disposed between the female and male ends thereof.

3. The fixation device of claim 2, wherein the catheter engagement portion of the elongate band comprises textured surfaces.

4. The fixation device of claim 3, wherein the textured surfaces comprise a plurality of spaced ribs.

5. The fixation device of claim 4, wherein the plurality of spaced ribs extend transversely across the elongate band.

6. The fixation device of claim 4, wherein the catheter engagement portion of the elongate band has a length sufficient to surround the catheter extending across the elongate band when the retention portion of the male end is received within the coupling opening of the female end.

7. The fixation device of claim 6, wherein the plurality of spaced ribs comprises at least three ribs configured to be distributed about a circumference of the catheter extending across the elongate band when the retention portion of the male end is received within the coupling opening of the female end.

8. The fixation device of claim 2, further comprising at least one catheter reception member extending laterally from the elongate band at the catheter engagement portion thereof, the at least one catheter reception member including a bore extending therethrough for reception of the catheter.

9. The fixation device of claim 8, wherein the at least one catheter reception member has an outwardly oriented frusto-conical shape.

10. The fixation device of claim 8, wherein the at least one catheter reception member includes a retention structure extending inwardly into the bore to engage the catheter inserted therethrough.

11. The fixation device of claim 10, wherein the retention structure has an annular configuration extending around the bore.

12. The fixation device of claim 8, wherein the at least one catheter reception member comprises first and second catheter reception portions disposed on opposite sides of the catheter engagement portion of the elongate band.

13. The fixation device of claim 1, wherein the retention portion of the male end including the laterally aligned side notches is a first retention portion, and wherein the male end further comprises a second retention portion.

14. The fixation device of claim 1, wherein the male end further includes an elongate neck portion disposed distally of the retention portion.

15. The fixation device of claim 14, wherein the male end at the elongate neck portion has a smaller width than at the retention portion.

16. The fixation device of claim 14, wherein the male end includes a tip disposed distally of the elongate neck portion having a larger width than at a width of the elongate neck portion.

17. The fixation device of claim 1, wherein the second suture opening extends through the male end of the elongate band distal to the side notches thereof.

18. The fixation device of claim 1, wherein the first and second suture openings are disposed at opposite ends of the elongate band.

* * * * *